US011977077B2

(12) United States Patent
Crnogorac-Jurcevic et al.

(10) Patent No.: US 11,977,077 B2
(45) Date of Patent: May 7, 2024

(54) BIOMARKERS FOR PANCREATIC CANCER

(71) Applicant: Queen Mary University of London, London (GB)

(72) Inventors: Tatjana Crnogorac-Jurcevic, London (GB); Tomasz Radon, London (GB)

(73) Assignee: Queen Mary University of London, London (GB)

( * ) Notice: Subject to any disclaimer, the term of this patent is extended or adjusted under 35 U.S.C. 154(b) by 518 days.

(21) Appl. No.: 17/003,139

(22) Filed: Aug. 26, 2020

(65) Prior Publication Data

US 2022/0042998 A1 Feb. 10, 2022

Related U.S. Application Data

(62) Division of application No. 15/548,240, filed as application No. PCT/GB2016/050277 on Feb. 5, 2016, now Pat. No. 10,782,301.

(30) Foreign Application Priority Data

Feb. 5, 2015 (GB) ..................... 1501930

(51) Int. Cl.
| | | |
|---|---|---|
| G01N 31/00 | (2006.01) | |
| C07K 16/28 | (2006.01) | |
| G01N 33/53 | (2006.01) | |
| G01N 33/574 | (2006.01) | |
| G16H 50/20 | (2018.01) | |
| G16H 50/30 | (2018.01) | |

(52) U.S. Cl.
CPC ....... *G01N 33/57438* (2013.01); *C07K 16/28* (2013.01); *G16H 50/20* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 9,551,035 B2* | 1/2017 | Schröder | G01N 33/57438 |
| 10,782,301 B2* | 9/2020 | Crnogorac-Jurcevic | C07K 16/28 |
| 11,726,090 B2* | 8/2023 | Schröder | G01N 33/57438 506/7 |
| 2006/0269921 A1 | 11/2006 | Segara et al. | |
| 2007/0031867 A1 | 2/2007 | Hoon | |
| 2007/0077582 A1 | 4/2007 | Slepnev | |
| 2007/0231822 A1 | 10/2007 | Mitas | |
| 2008/0306018 A1 | 12/2008 | Croce | |
| 2010/0092476 A1 | 4/2010 | Hanash et al. | |
| 2010/0144850 A1 | 6/2010 | Croce | |
| 2013/0317083 A1 | 11/2013 | Rigoutsos et al. | |
| 2014/0105824 A1 | 4/2014 | Shepard et al. | |
| 2014/0271621 A1 | 9/2014 | Hemken et al. | |
| 2014/0357515 A1 | 12/2014 | Friedrich | |
| 2015/0011414 A1 | 1/2015 | Johansen et al. | |
| 2015/0018230 A1 | 1/2015 | Murray et al. | |
| 2018/0274037 A1 | 9/2018 | Crnogorac-Jurcevic et al. | |
| 2019/0204323 A1 | 7/2019 | Crnogorac-Jurcevic et al. | |

FOREIGN PATENT DOCUMENTS

| | | |
|---|---|---|
| AU | 2016214140 A1 | 8/2017 |
| BR | 1120170168081 | 8/2017 |
| CA | 2974775 A1 | 8/2016 |
| CL | 42.015 | 3/2018 |
| CN | 107533062 A | 1/2018 |
| EP | 3254111 A1 | 12/2017 |
| EP | 3353324 | 8/2018 |
| HK | 1247276 | 9/2018 |
| IL | 253710 | 8/2020 |
| JP | 2006-500948 | 1/2006 |
| JP | 2013-516996 | 5/2013 |
| JP | 2018504609 A | 2/2018 |
| JP | 6786499 B2 | 11/2020 |
| KR | 10-2017-0129118 A | 8/2017 |
| MX | 2017009998 | 2/2018 |
| SG | 11201706223 | 8/2017 |
| WO | 2000034787 A1 | 6/2000 |
| WO | 2004099432 A2 | 11/2004 |
| WO | 2004102189 A1 | 11/2004 |
| WO | 2006024283 A2 | 3/2006 |
| WO | 2006081473 A2 | 8/2006 |
| WO | 2007098102 A2 | 8/2007 |
| WO | 2008036765 A2 | 3/2008 |
| WO | 2008063479 A2 | 5/2008 |
| WO | 2008136971 A1 | 11/2008 |
| WO | 2011137288 A2 | 11/2011 |
| WO | 2012100339 A1 | 8/2012 |
| WO | 2013040251 A2 | 3/2013 |
| WO | 2013107459 A2 | 7/2013 |
| WO | 2013152989 A2 | 10/2013 |
| WO | 2016124947 A1 | 8/2016 |
| WO | 2017051203 A1 | 3/2017 |

OTHER PUBLICATIONS

Zofia Von Marschall et al., International Journal of Oncology, vol. 27, No. 3, Sep. 1, 2005, pp. 669-679 (Year: 2005).*
Ghorai et al., miRNA gene counts in chromosomes vary widely in a species and biogenesis of miRNA largely depends on transcription or post-transcriptional processing of coding genes, 2014, Frontiers in Genetics, vol. 5, Article 100, 11 Pages.
Liang et al., Characterization of micoRNA expression profiles in normal human tissues, 2007, BMC Genomics, vol. 8 (166), 20 Pages.
Radon et al., Identification of a three-biomarker panel in urine for early detection of pancreatic adenocarcinoma, 2015, Clin. Cancer Res., vol. 21(15), pp. 3512-3521.

(Continued)

*Primary Examiner* — Lisa V Cook
(74) *Attorney, Agent, or Firm* — Nixon Peabody LLP; Linda B. Huber

(57) ABSTRACT

The present invention relates to pancreatic cancers and the use of biomarkers in biological samples for the diagnosis of such conditions, in particular pancreatic ductal adenocarcinoma. The biomarker panel comprises LYVE1, REG1 and TFF1. Methods of treatment are also provided, as well as kits useful in the diagnosis and treatment of pancreatic ductal adenocarcinoma. The present invention is particularly useful in detecting early-stage PDAC.

21 Claims, 13 Drawing Sheets

Specification includes a Sequence Listing.

(56) References Cited

OTHER PUBLICATIONS

JP 2017-541693 Office Action dated Jan. 8, 2020, 7 Pages.
Harada et al., Human REG I Gene is Up-Regulated in Intrahepatic Cholangiocarcinoma and its Precursor Lesions, 2001, Hepatology, vol. 33(5), 1036-1042.
Written Opinion of SG 11201706223V dated Apr. 10, 2018, 7 Pages.
Szafranska et al., MicroRNA Expression Alterations are Linked to Tumorigenesis and Non-Neoplastic Processes in Pancreatic Ductal Adenocarcinoma, 2007, Oncogene, vol. 26, pp. 4442-4452.
UK Search Report for GB 1517028.5 dated Jul. 8, 2016, 5 pages.
Mall et al., Stability of miRNA in human urine supports its biomarker potential, Biomark Med, 2013, 7(4), 17 pages.
Munding et al., Global microRNA expression profiling of microdissected tissues identifies miR-135b as a novel biomarker for pancreatic ductal adenocarcinoma, International Journal of Cancer, 2012, 131, E86-E95.
Eleventh Annual microRNA as Biomarkers and Diagnostics, Mar. 16-17, 2015 Program, 4 pages [accessed online on Mar. 6, 2015].
Tavano et al., Changes in miR-143 and miR-21 Expression and Clinicopathological Correlations in Pancreatic Cancers, Pancreas, 2012, 41(8):1280-1284.
Liu et al., Putative tumor suppressor gene SEL1L was downregulated by aberrantly upregulated has-mir-155 in human pancreatic ductal adenocarcinoma, Molecular Carcinogenesis, 2013, 53(9):711-721.
Debernardi et al., Noninvasive urinary miRNA biomarkers for early detection of pancreatic adenocarcinoma, Am J Cancer Res, 2015, 5(11):3455-3466.
International Search Report and Written Opinion for PCT/GB2016/052991 dated Feb. 13, 2017, 21 pages.
UK Search Report for GB1501930.0 dated Oct. 29, 2015, 1 page.
Tomita, Lymphatic Vessel Endothelial Hyaluronan Receptor 1 Immunocytochemical Staining For Pancreatic Islets and Pancreatic Endocrine Tumors, Pancreas, 2007, 35(4), e18-22.
Tomita, LYVE-1 Immunocytochemical Staining For Gastrointestinal Carcinoids, Pathology, 2009, 41(3), pp. 248-253.
Von Marschall et al., Vascular Endothelial Growth Factor-D Induces Lymphangiogenesis and Lymphatic Metastasis in Models of Ductal Pancreatic Cancer, International Journal of Oncology, 2005, vol. 27(3), pp. 669-679.
Roldo et al., MicroRNA Expression Abnormalities in Pancreatic Endocrine and Acinar Tumors are Associated with Distinctive Pathologic Features and Clinical Behavior, Journal of Clinical Oncology, 2006, vol. 24(29), pp. 4677-4684.
Porterfield et al., Discrimination between Adenocarcinoma and Normal Pancreatic Ductal Fluid by Proteomic and Glycomic Analysis, J. Proteome Res., 2014, vol. 13(2), pp. 395-407.
Nakata et al., MicroRNA-10b is Overexpressed in Pancreatic Cancer, Promotes Its Invasiveness and Correlates with a Poor Prognosis, Surgery, 2011, vol. 150(5), Abstract Only.
Arumugam et al., Trefoil Factor 1 Stimulates Both Pancreatic Cancer and Stellate Cells and Increases Metastasis, Pancreas, 2011, vol. 40(6), pp. 815-822.
International Search Report and Written Opinion for PCT/GB2016/050277 dated May 25, 2016, 15 pages.
Zoller, Pancreatic cancer diagnosis by free and exosomal miRNA, World Journal of Gastrointest Pathophysiol vol. 4(4), pp. 74-90.

* cited by examiner

| Urine | | Healthy (n=87) | CP (n=92) | PDAC (n=192) |
|---|---|---|---|---|
| | LYVE1 | 3.2 (5.3) / 0.51 (0.52) | 4.5 (9.6) / 0.49 (1.19) | 11.9 (16.5) / 2.04 (2.84) |
| | REG1A | 113.8 (261.8) / 16.3 (27.7) | 127.8 (349.9) / 14.8 (85.4) | 546.4 (1648.5) / 92.9 (242.7) |
| | REG1B | 31.1 (62.6) / 4.4 (6.2) (n=51) | 45.3 (104.4) / 4.2 (14.9) (n=42) | 124.2 (217.1) / 19.7 (46.0) (n=107) |
| | TFF1 | 2.2 (3.3) / 0.23 (0.46) | 2.8 (5.6) / 0.25 (0.80) | 3.7 (4.9) / 0.51 (0.91) |
| | Creatinine | 8.4 (6.3) / na | 7.7 (8.2) / na | 6.5 (6.8) / na |
| Plasma | | Healthy (n=28) | CP (n=50) | PDAC (n=147) |
| | CA19.9 | 8.7 (7.6) / na | 21.5 (38.1) / na | 399.0 (1281.2) / na |

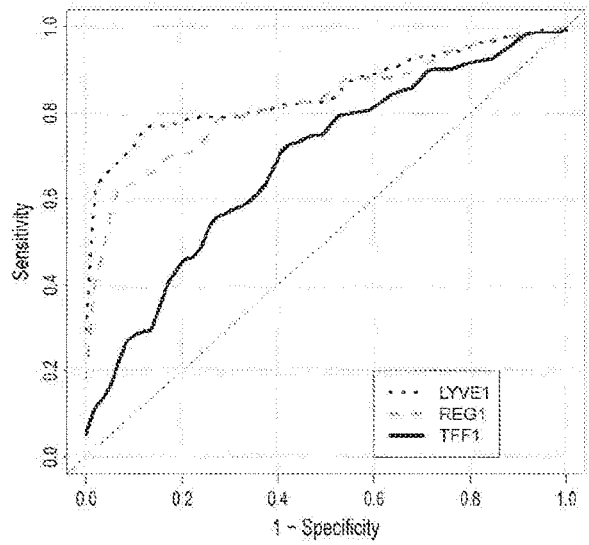
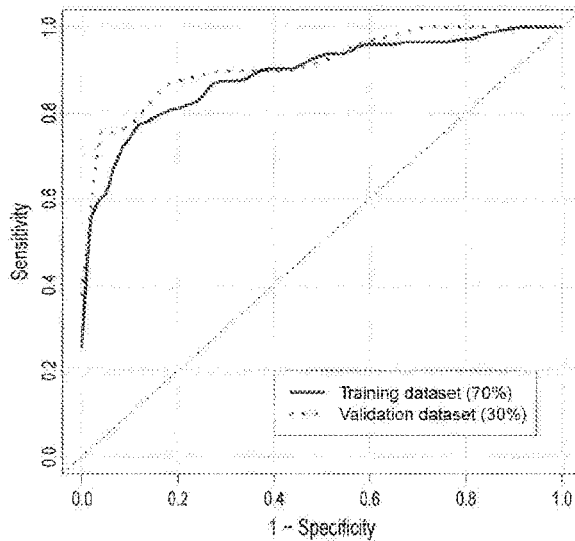
Fig. 2A    Fig. 2B
| Samples | Biomarkers | AUC (95% CI) | % SN (95% CI) at optimal cutpoint | % SP (95% CI) at optimal cutpoint |
|---|---|---|---|---|
| Training set (70%) | LYVE1 (cnorm) | 0.851 (0.801 - 0.902) | 76.9 (69.3 - 83.2) | 88.1 (79.6 - 96.6) |
| | REG1A (cnorm) | 0.823 (0.766 - 0.879) | 62.2 (53.8 - 69.9) | 94.9 (88.1 - 100.0) |
| | TFF1 (cnorm) | 0.686 (0.606 - 0.765) | 72.7 (65.0 - 79.7) | 59.3 (47.5 - 71.2) |
| | Panel (+ creat + age) | 0.891 (0.847 - 0.935) | 76.9 (69.9 - 83.2) | 89.8 (81.3 - 96.6) |
| Validation set (30%) | Panel (+ creat + age) | 0.921 (0.863 - 0.978) | 75.5 (63.3 - 87.8) | 100 (100.0 - 100.0) |
Fig. 2C

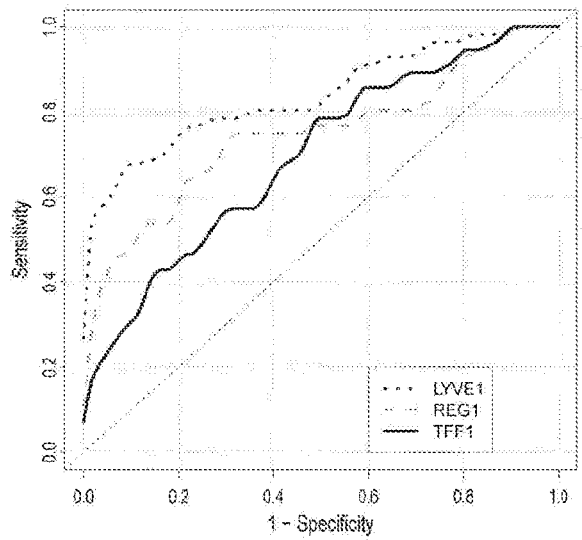
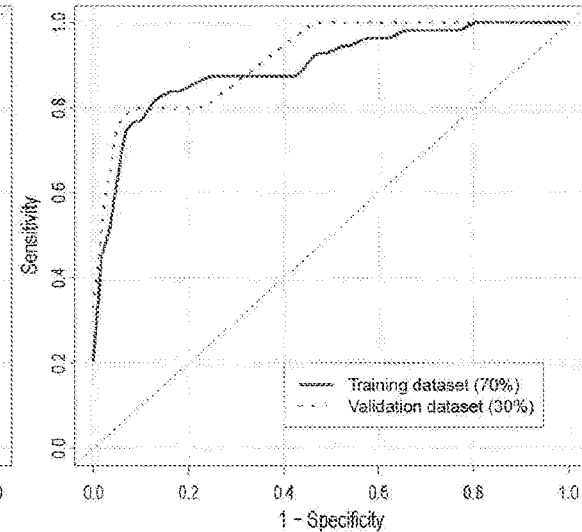
Fig. 4A    Fig. 4B
| Samples | Biomarkers | AUC (95% CI) | % SN (95% CI) at optimal cutpoint | % SP (95% CI) at optimal cutpoint |
|---|---|---|---|---|
| Training set (70%) | LYVE1 (cnorm) | 0.840 (0.767 - 0.914) | 67.9 (55.3 - 78.6) | 91.8 (83.6 - 98.4) |
| | REG1A (cnorm) | 0.748 (0.656 - 0.839) | 75.0 (64.3 - 85.7) | 68.9 (57.4 - 80.3) |
| | TFF1 (cnorm) | 0.696 (0.601 - 0.790) | 78.6 (67.8 - 89.3) | 52.5 (41.0 - 63.9) |
| | Panel (+ creat + age) | 0.900 (0.843 - 0.957) | 82.1 (71.4 - 91.1) | 88.5 (80.3 - 95.1) |
| Validation set (30%) | Panel (+ creat + age) | 0.926 (0.843 - 1.000) | 80.0 (60.0 - 100.0) | 76.9 (61.5 - 92.3) |
Fig. 4C

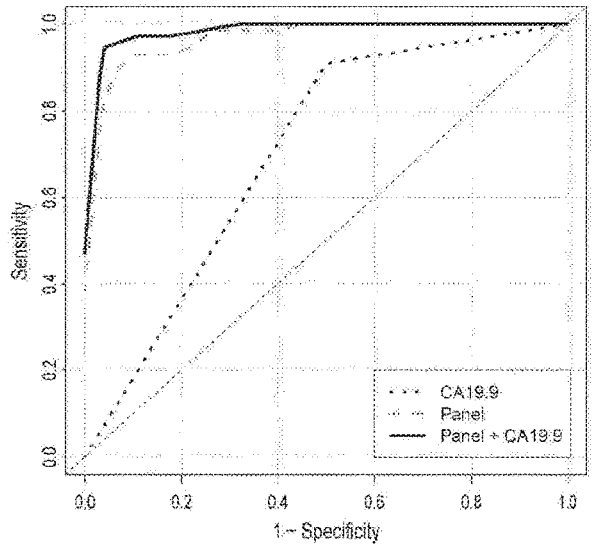
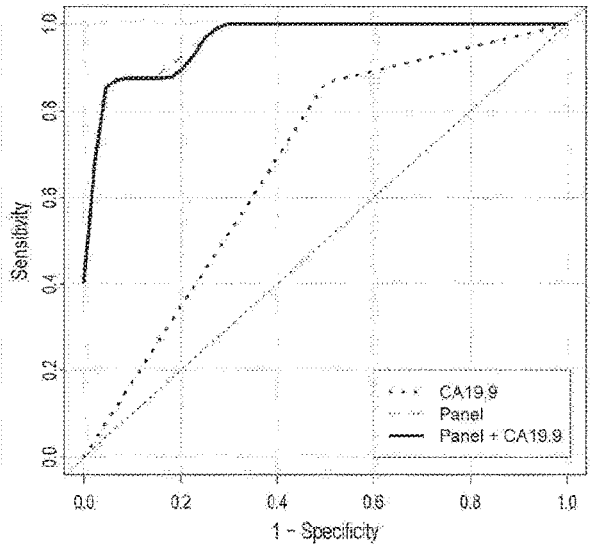
Fig. 5A  Fig. 5B
| Biomarkers | AUC (95% CI) | % SN (95% CI) at optimal cutpoint | % SP (95% CI) at optimal cutpoint |
|---|---|---|---|
| PDAC I-II vs Healthy | | | |
| Plasma CA19.9 (37U/mL) | 0.880 (0.814 - 0.945) | 83.1 (74.6 - 91.6) ^ | 92.9 (82.1 - 100) ^ |
| Panel | 0.973 (0.947 - 0.999) + | 93.0 (85.9 - 98.6) | 92.9 (82.1 - 100.0) |
| Panel + Plasma CA19.9 (37U/mL) | 0.991 (0.979 - 1.000) $ | 94.4 (88.7 - 98.6) | 100.0 (100.0 - 100.0) |
| PDAC I-IIA vs Healthy | | | |
| Plasma CA19.9 (37U/mL) | 0.839 (0.719 - 0.959) | 75.0 (56.3 - 93.8) | 92.9 (82.1 - 100.0) |
| Panel | 0.971 (0.929 - 1.000) ++ | 87.5 (68.8 - 100.0) | 96.4 (89.3 - 100.0) |
| Panel + Plasma CA19.9 (37U/mL) | 0.969 (0.924 - 1.000) $$ | 87.5 (68.8 - 100.0) | 96.4 (89.3 - 100.0) |
Fig. 5C

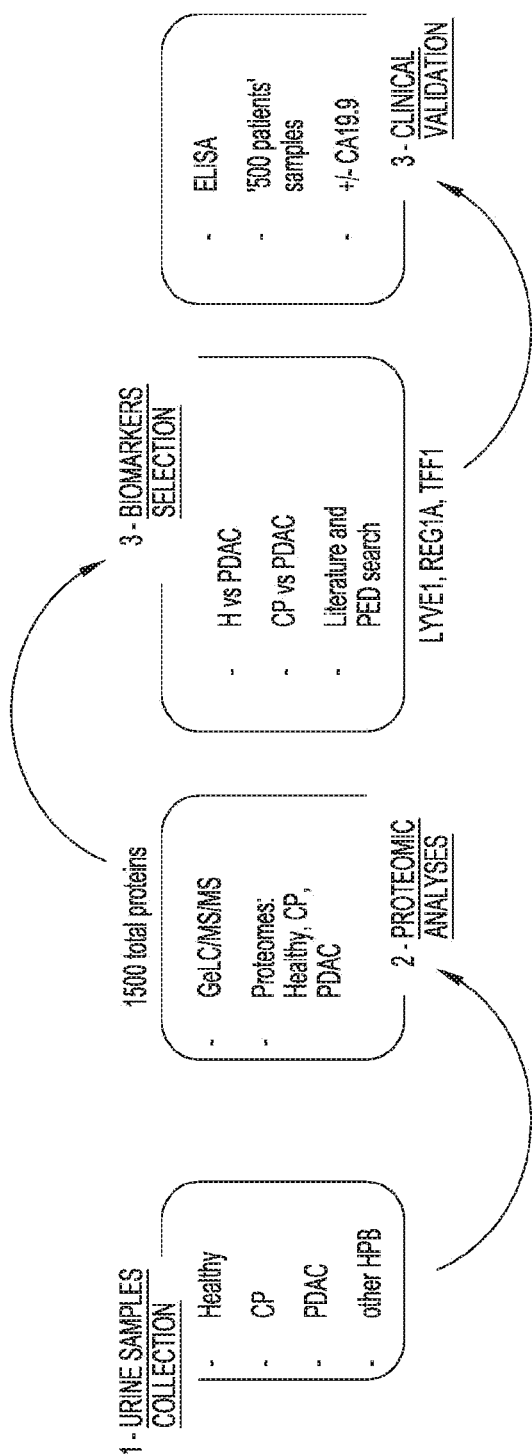
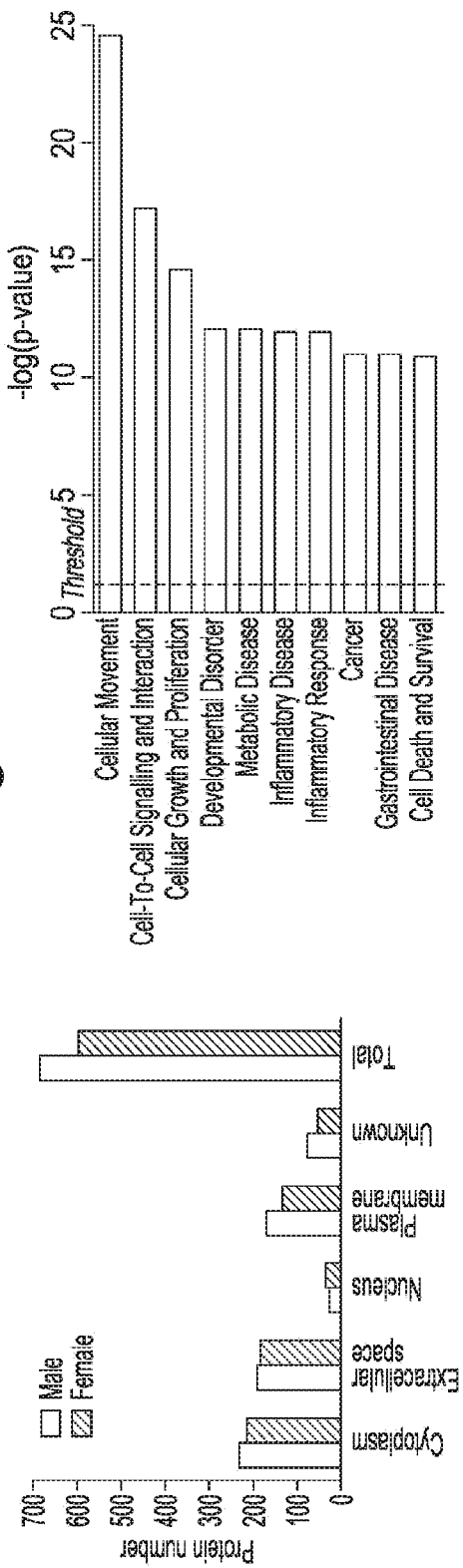
Fig. 6A
Fig. 6B
Fig. 6C

|  | CA19.9p | LYVE1 | REG1A |
|---|---|---|---|
| Healthy | | | |
| LYVE1 | -0.15 (NS) | | |
| REG1A | -0.38* | 0.35*** | |
| TFF1 | -0.12 (NS) | 0.0004 (NS) | 0.07 (NS) |
| CP | | | |
| LYVE1 | 0.17 (NS) | | |
| REG1A | 0.12 (NS) | 0.61*** | |
| TFF1 | -0.13 (NS) | 0.25* | 0.35*** |
| PDAC | | | |
| LYVE1 | 0.13 (NS) | | |
| REG1A | 0.18* | 0.53*** | |
| TFF1 | 0.03 (NS) | 0.51*** | 0.51*** |

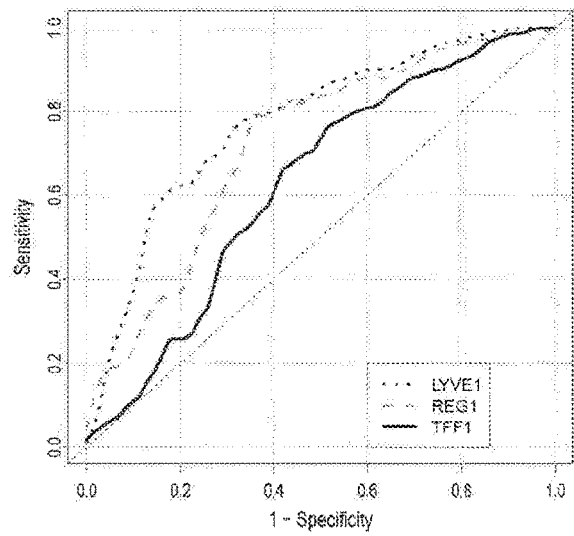
Fig. 8A
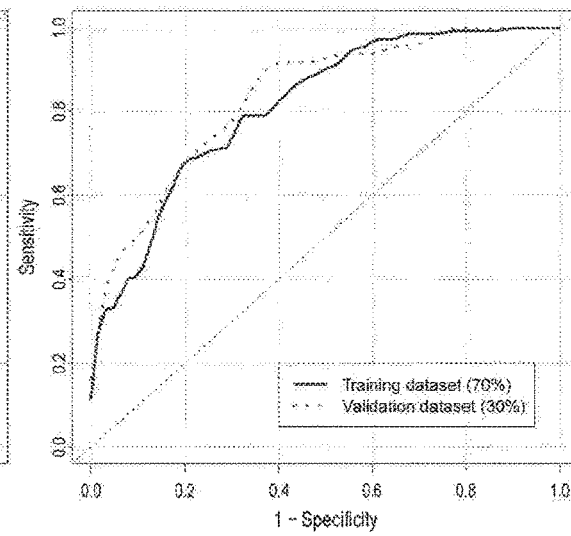
Fig. 8B
| Samples | Biomarkers | AUC (95% CI) | % SN (95% CI) at optimal cutpoint | % SP (95% CI) at optimal cutpoint |
|---|---|---|---|---|
| Training set (70%) | LYVE1 (cnorm) | 0.775 (0.704 - 0.846) | 76.9 (69.9 - 83.2) | 69.4 (58.1 - 80.7) |
| | REG1A (cnorm) | 0.722 (0.643 - 0.801) | 78.3 (71.3 - 84.6) | 66.1 (54.8 - 77.4) |
| | TFF1 (cnorm) | 0.629 (0.540 - 0.717) | 76.2 (68.5 - 83.2) | 50.0 (37.1 - 61.3) |
| | Panel (+ creat + age) | 0.815 (0.752 - 0.878) | 68.5 (60.1 - 76.2) | 80.6 (71.0 - 90.3) |
| Validation set (30%) | Panel (+ creat + age) | 0.839 (0.751 - 0.928) | 67.4 (53.1 - 79.6) | 80.0 (63.3 - 93.3) |
Fig. 8C

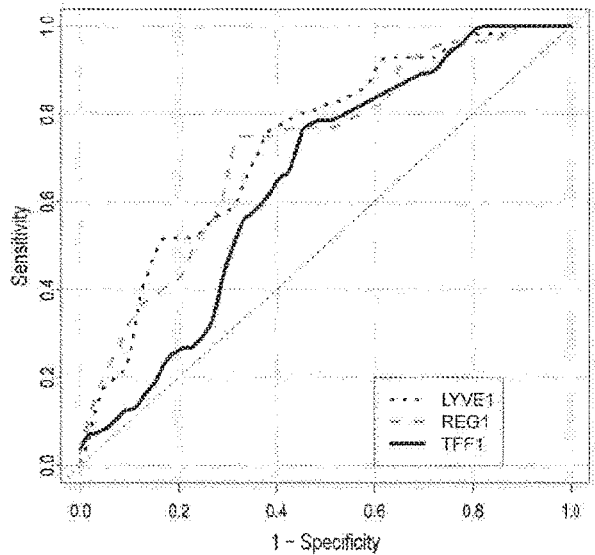
Fig. 8D
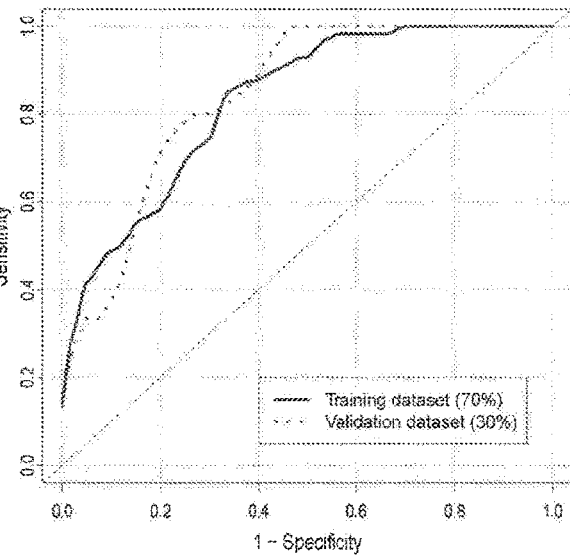
Fig. 8E
| Samples | Biomarkers | AUC (95% CI) | % SN (95% CI) at optimal cutpoint | % SP (95% CI) at optimal cutpoint |
|---|---|---|---|---|
| Training set (70%) | LYVE1 (cnorm) | 0.732 (0.644 - 0.821) | 76.8 (66.1 - 87.5) | 62.1 (50.0 - 74.3) |
| | REG1A (cnorm) | 0.723 (0.633 - 0.813) | 75.0 (62.5 - 85.7) | 69.7 (57.6 - 80.3) |
| | TFF1 (cnorm) | 0.650 (0.553 - 0.748) | 76.8 (64.3 - 87.5) | 56.1 (43.9 - 68.2) |
| | Panel (+ creat + age) | 0.831 (0.762 - 0.901) | 85.7 (75.0 - 94.6) | 66.7 (56.1 - 78.8) |
| Validation set (30%) | Panel (+ creat + age) | 0.846 (0.730 - 0.963) | 100.0 (100.0 - 100.0) | 50.0 (30.8 - 69.2) |
Fig. 8F

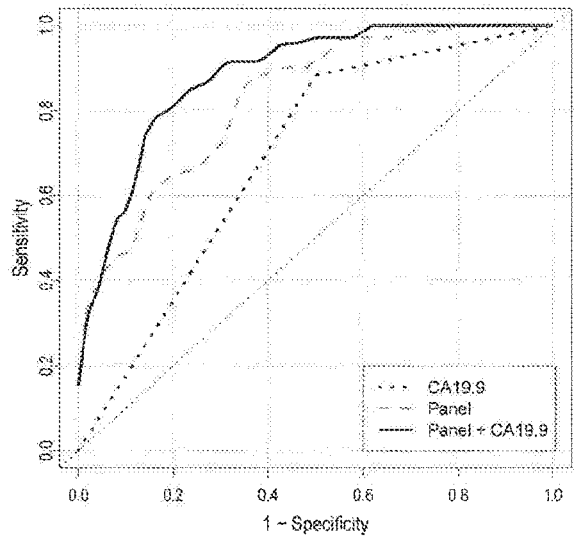
Fig. 9A
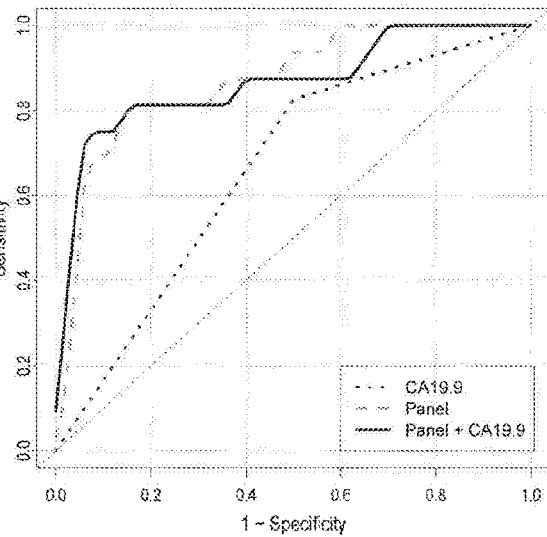
Fig. 9B
| Biomarkers | AUC (95% CI) | % SN (95% CI) at optimal cutpoint | % SP (95% CI) at optimal cutpoint |
|---|---|---|---|
| CP vs PDAC I-II | | | |
| Plasma CA19.9 (37U/mL) | 0.775 (0.699 - 0.852) | 83.1 (74.6 - 91.6) ^ | 72.0 (60.0 - 84.0) ^ |
| Panel | 0.830 (0.759 - 0.902) + | 87.3 (78.8 - 94.4) | 66.0 (52.0 - 78.0) |
| Panel + Plasma CA19.9 (37U/mL) | 0.885 (0.825 - 0.945) $ | 77.5 (67.6 - 87.3) | 86.0 (76.0 - 94.0) |
| CP vs PDAC I-IIA | | | |
| Plasma CA19.9 (37U/mL) | 0.735 (0.609 - 0.861) | 75.0 (56.3 - 93.8) | 72.0 (60.0 - 84.0) |
| Panel | 0.871 (0.770 - 0.972) ++ | 81.2 (62.5 - 100.0) | 86.0 (76.0 - 94.0) |
| Panel + Plasma CA19.9 (37U/mL) | 0.866 (0.749 - 0.984) $$ | 75.0 (56.3 - 93.8) | 94.0 (88.0 - 100.0) |
Fig. 9C

|  | IPMN | AMP | NET | CHL | DuCa |
|---|---|---|---|---|---|
| Cases (n) | 33 | 26 | 18 | 24 | 16 |
| Gender | M=21 | M=13 | M=9 | M=17 | M=4 |
|  | F=12 | F=13 | F=9 | F=7 | F=12 |
| Age range (Median) | 27 - 83 (66) | 41 - 78 (68) | 42 - 78 (63) | 20 - 79 (54) | 46 - 77 (65) |

Fig. 10A

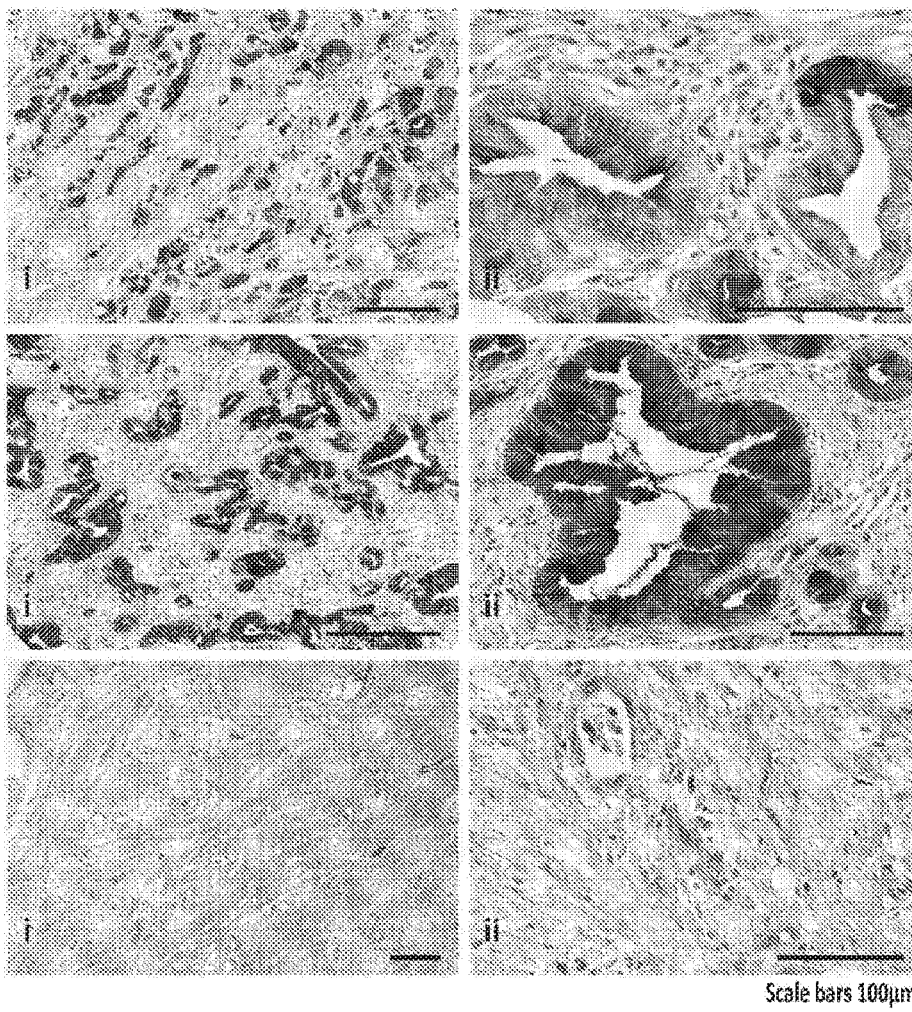
Fig. 11A
Fig. 11B
Fig. 11C
Scale bars 100μm
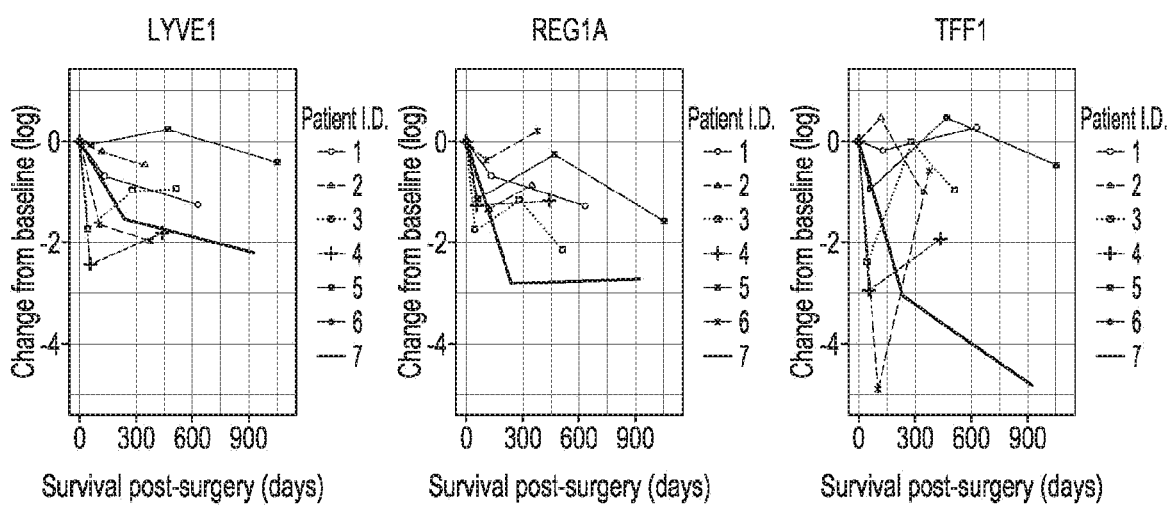
Fig. 11D

BIOMARKERS FOR PANCREATIC CANCER

CROSS-REFERENCE TO RELATED APPLICATIONS

This application is a Divisional of U.S. application Ser. No. 15/548,240, filed Aug. 2, 2017, now U.S. Pat. No. 10,782,301, which is a National Phase of International Application No. PCT/GB2016/050277, filed Feb. 5, 2016, which designated the U.S. and that International Application was published under PCT Article 21(2) in English. This application also includes a claim of priority under 35 U.S.C. § 119(a) and § 365(b) to British patent application No. GB 1501930.0 filed Feb. 5, 2015, the entirety of which is herein incorporated by reference.

The present invention relates to pancreatic cancers and the use of biomarkers in biological samples for the diagnosis of such conditions, in particular pancreatic ductal adenocarcinoma.

Pancreatic ductal adenocarcinoma (PDAC) is the most common exocrine pancreatic malignancy accounting for more than 80% of malignant neoplasms arising in pancreas. It is the fourth most common cause of cancer-related deaths in the Western world. When diagnosed, the majority of patients display locally advanced disease or have established metastases, therefore surgery is possible in only 10-20% of patients (Sener et at (1999) *J Am Coll Surg*, 189:1-7). While the overall 5-year survival rate is less than 5%, the 5-year survival in patients after surgical resection and adjuvant chemotherapy can reach 30%.

Pancreatic ductal adenocarcinoma (PDAC) is one of the rare cancers for which no significant improvements in the diagnostic and therapeutic approaches have been made in the last decades. Despite considerable progress in our understanding of the disease at the molecular level, novel findings have not yet reached the clinic, and the majority of patients are still faced with a grim average survival of 5 to 6 months. With over 38,000 PDAC-related deaths in the US and over 40,000 in Europe in 2013, this malignancy is currently the fourth leading cause of cancer-related death, but predicted to become the second by 2030.

PDAC is one of the most challenging cancers to detect. The retroperitoneal position of the pancreas, a number of complex underlying molecular abnormalities, and the lack of specific clinical symptoms result in a majority of patients presenting at an advanced stage. Fewer than 20% of patients can thus undergo potentially curative surgery, while the remaining ones can only be offered palliative treatment.

These worrying figures would change significantly with improved tool(s) for early detection, as 5-year survival approaching 70% has been reported after incidental diagnosis of stage I PDAC tumours, when they were still confined to the pancreas with a size <2 cm. Importantly, a considerable 'window' of opportunity of around a decade exists for earlier diagnosis (Yachida S, et al. (2010) *Nature* 467(7319): 1114-1117). Detection at an early stage is also crucial given the poor efficacy of current therapies for metastatic disease, when potentially curative surgery is no longer feasible.

Timely detection of PDAC is, however, hampered by several factors: lack of specific clinical symptoms in the early stage of the disease, insufficient sensitivity of current imaging modalities and, despite intensive efforts, lack of accurate body fluid-based biomarkers of early-stage disease (for a review see Kaur et al. (2012) *Biomark Med* 6(5):597-612.). Early stage PDAC is also difficult to differentiate from chronic pancreatitis (CP), a benign inflammatory disease of the pancreas and one of the risk factors for PDAC. Serum carbohydrate antigen 19.9 (CA19.9), the only PDAC biomarker in widespread clinical use at present, suffers from false negative results in patients with Lewis-negative genotype, poor positive predictive value in the asymptomatic population and low sensitivity (79%-81%) in symptomatic patients. Less than 50% of cases with early disease (tumour <2 cm) have raised CA19-9 levels, yet CA19.9 levels may be elevated in various other benign and malignant pancreatic and hepato-biliary diseases (including chronic pancreatitis), as well as in unrelated cystic and inflammatory diseases (for review see Ballehaninna U K, Chamberlain R S, "Serum CA 19-9 as a Biomarker for Pancreatic Cancer-A Comprehensive Review", *Indian J Surg Oncol*, 2011; 2:88-100). In addition, Lewis a/b antigen (which Ca19.9 recognizes) is not expressed in around 10% of population Proteomic techniques have recently been used to study protein expression in pancreatic cancer tissue, pancreatic juice and serum/plasma specimens (see, for example, Koomen et al. (2005) *Clin Cancer Res*, 11:1110-1118), but none of these have, as yet, resulted in the discovery of biomarkers suitable for clinical practice.

Recently, urine was studied as a potential source of biomarkers as it is an easily and non-invasively obtained bio-fluid (Pieper et at (2004) *Proteomics*, 4:1159-1174). In comparison with plasma, urine proteins are less complex and more thermostable. Furthermore, most common proteins (albumin, uromodulin) comprise a lesser proportion of the urinary proteome, so sample processing requires less pre-cleaning/fractionation. Approximately 49% of urinary proteins are soluble products of glomerular filtration of plasma (Barret et at (2007) *Cmaj*, 177:361-368), and therefore a substantial number of proteins in urine arise from extrarenal sources (Thongboonkerd et al. (2005) *Curr Opin Nephrol Hypertens*, 14:133-139).

In addition to urological cancers, several cancer-related proteins have been identified in the urine of patients with lung, ovarian and breast cancers.

WO2004/102189 describes biomarkers for the diagnosis pancreatic cancer. Serum samples from patients with pancreatic cancer were compared with serum samples from healthy donors and the resulting biomarkers characterized by their weight. A similar approach was carried out in WO2004/099432, which provides further biomarkers for detecting pancreatic cancer. WO2000/34787 describes methods of diagnosing epithelial cancers involving the measurement of the levels of biomarkers in urine There are currently no specific and sensitive biomarkers for early diagnosis of pancreatic adenocarcinoma. This is extremely important, as if pancreatic adenocarcinoma can be detected early (e.g. stage I), the survival of such patients can be greatly improved (currently, most patients are diagnosed at stage III/IV with a 5-year survival rate of <5%). Highly accurate biomarkers for early detection are thus expected to significantly impact on a patient's prognosis.

There is therefore a need for a sensitive and specific panel of markers that would enable not only early diagnosis of PDAC, but also aid in differentiating between PDAC and other tumours, as well as between PDAC and chronic pancreatitis (CP). Preferably the markers will be detectable in a sample that is easy and non-invasive to obtain and is sensitive enough to detect the disease during its early stages.

SUMMARY OF THE INVENTION

In a first aspect of the invention there is provided a biomarker panel useful in the diagnosis of pancreatic ductal adenocarcinoma (PDAC), the panel comprising LYVE1, REG1 and TFF1. References to REG1 herein include REG1A and REG1B. In some embodiments, the panel may further comprise CA19.9.

In a second aspect of the invention there is provided a method of screening or testing for pancreatic ductal adenocarcinoma (PDAC) comprising detecting the level of expression or concentration of a protein selected from the group consisting of LYVE1, REG1 (for example REG1A and/or REG1B) and TFF1, or combinations thereof, in a biological sample. In some embodiments, the biological sample is a urine sample.

In a third aspect of the invention there is provided a protein selected from the group consisting of LYVE1, REG1 (for example REG1A and/or REG1B) and TFF1, or a combination thereof, for use in diagnosing pancreatic ductal adenocarcinoma. There is also provided the use of a protein selected from the group consisting of LYVE1, REG1 (for example REG1A and/or REG1B) and TFF1 in methods of detecting or diagnosing PDAC.

In a fourth aspect of the invention there is provided a kit for testing for pancreatic ductal adenocarcinoma comprising a means for detecting the level of expression or concentration of LYVE1, REG1 (for example REG1A and/or REG1B) or TFF1, or combinations thereof, in a biological sample.

In a further aspect of the invention there is provided a method of distinguishing between PDAC and chronic pancreatitis, comprising detecting the level of expression of LYVE1, REG1 (for example REG1A and/or REG1B) and/or TFF1 in a urine sample. The method may comprise comparing the expression levels of each of the proteins with a reference.

In a further aspect of the invention there is provided a method of detecting or diagnosing early stage PDAC, for example stage I or stage II PDAC, comprising detecting the level of expression or concentration of the biomarker panel proteins LYVE1, REG1 (REG1A and/or REG1B) and/or TFF1 in a biological sample. The method may further comprise comparing the expression levels or concentration of each of the quantified proteins with a reference.

In a still further aspect of the invention there is provided a method of treating PDAC in a patient, comprising detecting the level of expression or concentration of a protein selected from the group consisting of LYVE1, REG1 (for example REG1A and/or REG1B) and TFF1, or combinations thereof, in a biological sample, optionally comparing the level of expression with a control/reference, and proceeding with treatment for PDAC if PDAC is diagnosed or suspected. Methods of prognosis are also included in the present invention, comprising determining the level of expression or concentration of one or more proteins selected from the group consisting of LYVE1, REG1 (for example REG1A and/or REG1B) and TFF1 in a biological sample, optionally comparing the level of expression with a control/reference, and determining the prognosis for the patient.

In embodiments of the invention, the biomarkers used in the invention can be used separately (i.e. only one of LYVE1, REG1 (for example REG1A and/or REG1B) and TFF1), they can be used in pairs (e.g. LYVE1 and REG1 (for example REG1A and/or REG1B), LYVE1 and TFF1, or REG1 (for example REG1A and/or REG1B) and TFF1), three biomarkers might be used together (each of LYVE1 and TFF1 and one of REG1A or REG1B), or all tour may be used (LYVE1, TFF1, REG1A and REG1B). A fifth biomarker, CA19.9 may also be used. In embodiments of the invention, the level of expression of LYVE1, REG1 (for example REG1A and/or REG1B) and/or TFF1 may be determined by quantifying gene expression (for example quantifying mRNA in a biological sample), or by quantifying protein expression (for example quantifying protein concentration in a biological sample).

BRIEF DESCRIPTION OF THE FIGURES

Reference is made to a number of Figures as follows:

FIG. 2—Diagnostic performance of urine biomarkers in discriminating pancreatic adenocarcinoma patients from healthy controls. A, ROC curves of PDAC (n=143) versus healthy (n=59) subjects for individual creatinine-normalised urine biomarkers in the training set (70% of the data); B, ROC curves of PDAC versus healthy for the panel in the training set and in the independent validation set (30% of the data: PDAC n=49, healthy n=28): C, Summary table. AUC: area under the curve, SN: sensitivity, SR specificity, with corresponding 95% Confidence Intervals (CI). SN and SP in the validation set are derived for optimal cut point determined in the training dataset. cnorm: creatinine-normalised, creat: creatinine.

FIG. 4—Diagnostic performance of urine biomarkers in discriminating early pancreatic adenocarcinoma patients form healthy individuals. A, ROC curves of stages I-II PDAC (n=56) versus healthy (n=61) subjects for individual urine biomarkers in the training set (70% of the data); B, ROC curves of stage I-II PDAC versus healthy for the panel in the training set and in the independent validation set (30% of the data; PDAC n=15, healthy n=26); C, Summary table. AUC: area under the curve, SN: sensitivity, SP: specificity, with corresponding 95% Confidence Intervals (CI). SN and SP in the validation set are derived for optimal cutpoint determined in the training dataset. cnorm: creatinine-normalised, creat: creatinine.

FIG. 5—Diagnostic performance of the urine biomarker panel and CA19.9 in discriminating early pancreatic adenocarcinoma patients form healthy individuals. A, ROC curves of the biomarker panel with corresponding plasma CA19.9 alone and in combination comparing healthy urine (n=28), and urines from PDAC stages I-II, n=71 and I-IIA, n=16 (B). C, Summary table, AUC: area under the curve, SN: sensitivity, SP: specificity with 95% Confidence Interval (CI). SN and SP in the validation set were derived for optimal cutpoint determined in the training dataset.

Legend for FIG. 5C
^Optimal cutpoint for CA19.9 is 37 U/mL
+ DeLong's 1-sided test for correlated/paired AUCs to assess whether the urine panel gives a significantly greater AUC compared to plasma CA19.9 alone used as a dichotomous biomarker (0.973 versus 0.880), p=0.005

$ DeLong's 1-sided test for correlated/paired AUCs to assess whether the addition of plasma CA19.9 used as a dichotomous biomarker significantly increase the AUC over the urine panel alone (0.991 versus 0.973), p=0.04

++ DeLong's 1-skied test for correlated/paired AUCs to assess whether the urine panel gives a significantly greater AUC compared to plasma CA19.9 alone used as a dichotomous biomarker (0.971 versus 0.839), p=0.006

$$ DeLong's 1-sided test for correlated/paired AUCs to assess whether the addition of plasma CA19.9 used as a dichotomous biomarker significantly increase the RUC over the urine panel alone (0.969 versus 0.971), p=0.7

FIG. 6—Urine proteome analysis. A, schematic outline of the study; B, classification of total identified proteins according to sub-cellular localisation; and C, functional activity determined by Ingenuity Pathway Analysis. H: healthy, CP: chronic pancreatitis, PDAC: pancreatic ductal adenocarcinoma, GeLC/MS/MS: SDS-PAGE-Liquid Chromatography-Tandem Mass Spectrometry.

Figures 7A, 7B:
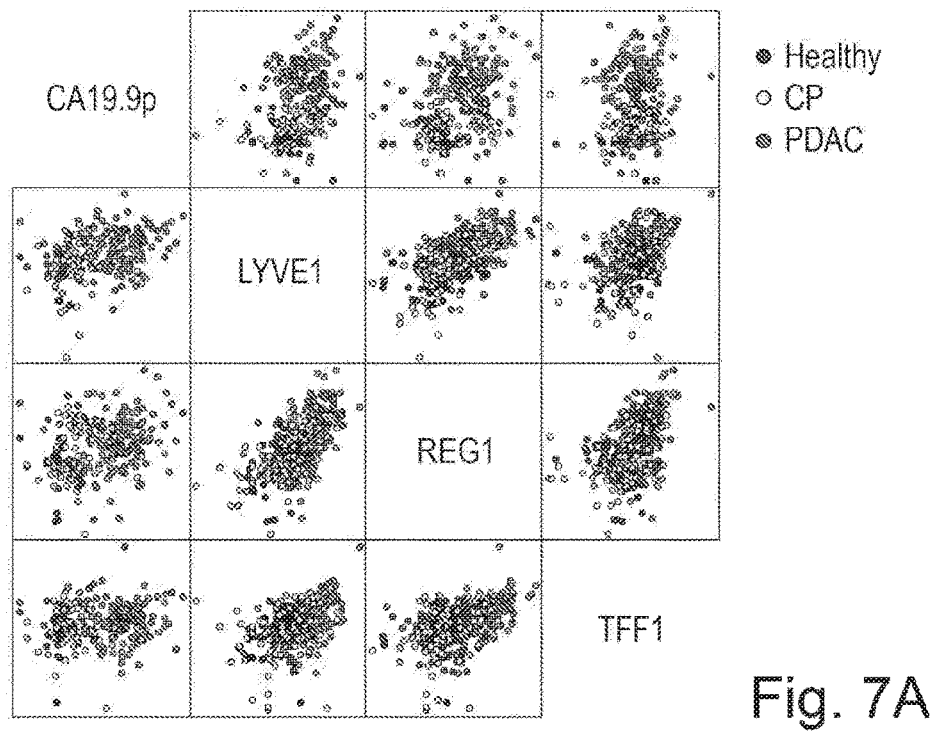

FIG. 7—Correlation of the three urinary biomarkers and plasma CA19.9 (CA19.9p). A, Correlation plots (Navy blue/darkest: Healthy; Turquoise/lightest: chronic pancreatitis (CP); Purple/intermediate: pancreatic adenocarcinoma (PDAC), B, Pearson correlation coefficients and corresponding significance (NS: non-significant, *: P<0.05, : P<0.01, *: P<0.001

FIG. 8—Diagnostic performance of urine biomarkers in discriminating pancreatic adenocarcinoma all stages (A-C) and stage I-II (D-F) from chronic pancreatitis patients. A, ROC curves of PDAC (n=143) versus CP (n=62) patients for individual urine biomarkers in the training set (70% of the data). B, ROC curves of PDAC versus CP patients for the panel in the training set and in the independent validation set (30% of the data, PDAC n=49, CP n=30). C, Summary table. D, ROC curves of individual urine biomarkers in training dataset (70%, PDAC n=56, CP=66). E, ROC curves of the panel in training and validation (PDAC n=15, CP n=26) dataset. F, Summary table. Cnorm, creatinine-normalised, creat, creatinine, AUC: area under the curve SN: sensitivity, SP: specificity. with 95% Confidence Interval (CI). SN and SP in the validation set were derived for optimal cutpoint determined in the training dataset.

FIG. 9—Exploratory comparison of plasma CA19.9 and the urine biomarker panel in discriminating early pancreatic adenocarcinoma from chronic pancreatitis patients. A. ROC curves of the biomarker panel with corresponding plasma CA19.9 alone and in combination comparing CP urine (n=50), and urines from PDAC stages I-II (n=71) and I-IIA (n=16) (B). C, Summary table. AUC: area under the curve, SN: sensitivity, SP: specificity with 95% Confidence Interval (CI). SN and SP in the validation set were derived for optimal cutpoint determined in the training dataset.

Legend for FIG. 9C

^Optimal cutpoint for CA19.9 is 37 U/mL

+ DeLong's 1-sided test for correlated/paired AUCs to assess whether the urine panel gives a significantly greater AUC compared to plasma CA19.9 alone used as a dichotomous biomarker (0.830 versus 0.775), p=0.1

$ DeLong's 1-sided test for correlated/paired AUCs to assess whether the addition of plasma CA19.9 used as a dichotomous biomarker significantly increase the AUC over the urine panel alone (0.885 versus 0.830), p=0.01

++ DeLong's 1-sided test for correlated/paired AUCs to assess whether the urine panel gives a significantly greater AUC compared to plasma CA19.9 alone used as a dichotomous biomarker (0.871 versus 0.735), p=0.004

$$ DeLong's 1-sided test for correlated/paired AUCs to assess whether the addition of plasma CA19.9 used as a dichotomous biomarker significantly increase the AUC over the urine panel alone (0.868 versus 0.871), p=0.6

Figure 10B:
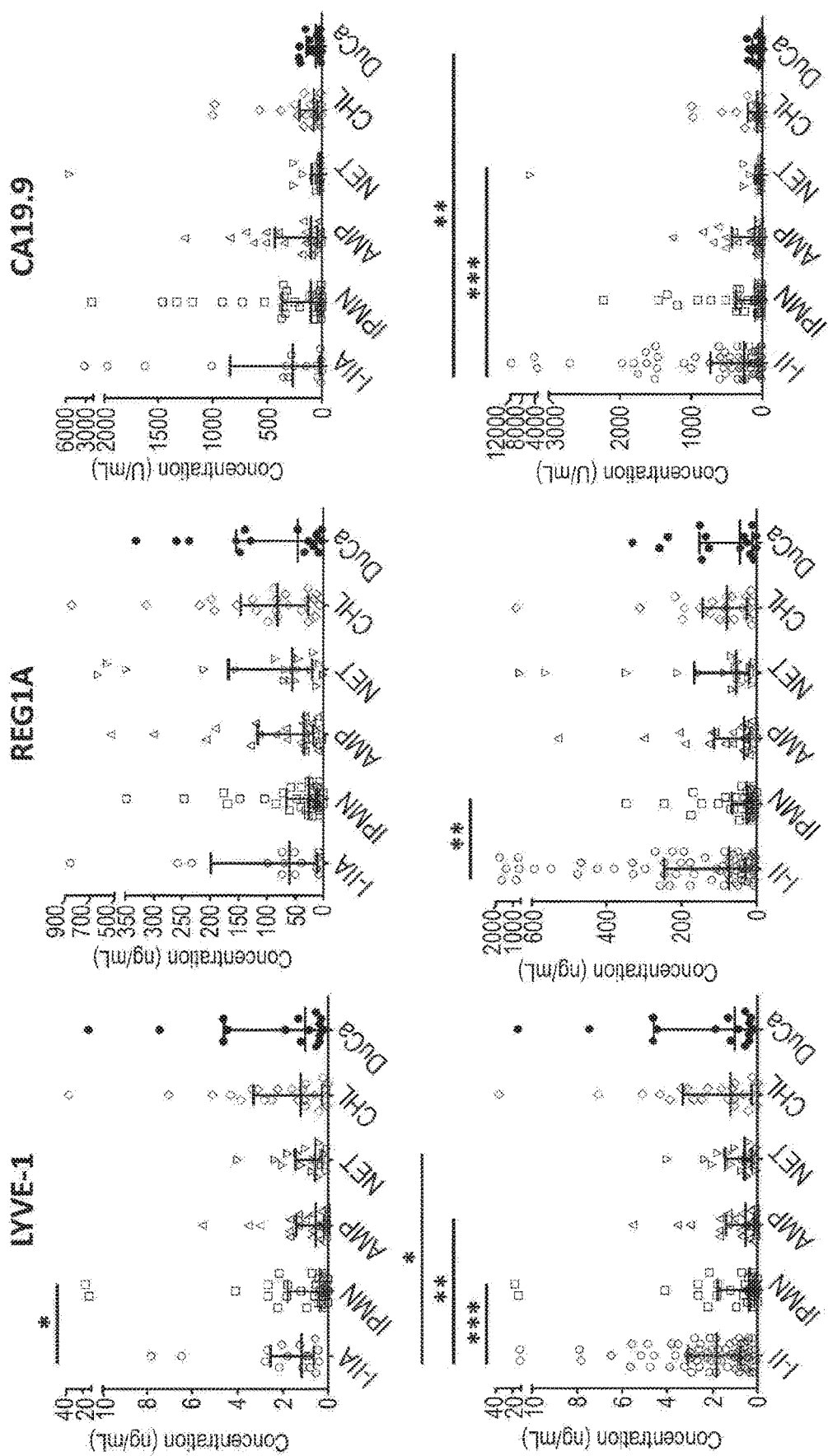

FIG. 10—Urine biomarker concentrations in different tumours. A, Demographic details. B. Scatter dot plots of urine LYVE1, REG1A and plasma CA19.9 in different hepatobiliary pathologies and early stages of pancreatic adenocarcinoma (I-IIA, n=16) and I-II (n=71). The level of TFF1 protein was not measured in these samples due to substantial modifications made to the original ELISA assay by the source company at the moment of this analysis. IPMN (n=33): intraductal papillary mucinous neoplasm, AMP (n=26): ampullary cancer, NET (n=18): neuroendocrine tumour, CHL (n=24): cholangiocarcinoma, DuCA (n=16): duodenal cancer. Bars indicate median and IQR values. Upper bars: Kruskal-Wallis/Dunn's post test, *: P<0.5, : P<0.01, *: P<0.001; where not shown, difference not statistically significant.

FIG. 11—Expression of the biomarker panel proteins in pancreatic cancer tissues. A, Immunohistochemical analysis of REG1A: i) REG1A in poorly differentiated PDAC, ii) luminal REG1A in malignant glands. B, TFF1: i) heterogenous expression in cancer, ii) luminal TFF1 in malignant gland. C, LYVE1 expression in the scattered lymphatic vessels i) in the muscle layer and ii) in the stroma surrounding malignant gland. D, The biomarker levels during monitoring of pancreatic adenocarcinoma patients: LYVE1, REG1A and TFF1 were measured using ELISA in urine samples collected before surgery and during the patients' follow up. Each point represents log-transformed ELISA values at a particular time point (x-axis).

DETAILED DESCRIPTION OF THE INVENTION

Biomarker Panels

The present invention provides a biomarker panel useful in the diagnosis of pancreatic ductal adenocarcinoma (PDAC), the panel comprising LYVE1, REG1 (REG1A and/or REG1B) and TFF1. In particular, the present invention provides a method of diagnosing, screening or testing for pancreatic ductal adenocarcinoma (PDAC) comprising detecting or level of expression of a gene or protein selected from the group consisting of LYVE1, REG1 (REG1A and/or REG1B) and TFF1, or combinations thereof, in a biological sample. In preferred embodiments, at least two of LYVEI, REG1 and TFF1 are used. In a more preferred embodiment, all three are used.

LYVE1 is also known as lymphatic vessel endothelial hyaluronan receptor and extracellular link domain containing 1 (XLKD1) is a type I integral membrane glycoprotein. The encoded protein acts as a receptor and binds to both soluble and immobilized hyaluronan. References to LYVE include NCBI (GenBank) reference sequence transcript NM_006691.3 (GI:15130120), NCBI protein ID NP_006682.2 (GI:40549451), GeneID:10894, and HGNC (HUGO (Human Gene Organisation) Gene Nomenclature Committee gene ID):14687. The gene has 4 splice variants; two are protein coding (full length protein has 322 amino acids, and the second one 218 amino acids). The full sequence of the protein is as follows:

(SEQ ID NO: 1)
MARCFSLVLLLTSIWTTRLLVQGSLRAEELSIQVS

CRIMGITLVSKKANQQLNFTEAKEACRLLGLSLAG

KDQVETALKASFETCSYGWVGDGFVVISRISPNPK

CGKNGVGVLIWKVPVSRQFAAYCYNSSDTWTNSCI

PEIITTKDPIFNTQTATQTTEFIVSDSTYSVASPY

STIPAPTTTPPAPASTSIPRRKKLICVTEVFMFTS

TMSTETEPFVENKAAFKNEAAGFGGVPTALLVLAL

LFFGAAAGLGFCYVKRYVKAFPFTNKNQQKEMIET

KVVKEEKANDSNPNEESKKTDKNPEESKSPSKTTV

RCLEAEV

REG1A refers to regenerating islet-derived protein 1 that belongs to a family of REG (regenerating) glycoproteins, which are expressed in pancreatic acinar cells and act as both autocrine and paracrine growth factors. The Reg gene family is a multigene family grouped into four subclasses, types I, II, III and IV; REG1A gene is a type I subclass member. Other family members: REG1B, REGL, PAP and this gene are tandemly clustered on chromosome 2p12 and may have arisen from the same ancestral gene by gene duplication. REG1A encodes a protein that is secreted by the exocrine pancreas. References to REG1 herein include two commonly described genes, i.e. REG1A and REG1B, whose products are more than 80% identical at the protein level, and are difficult to distinguish. Hence in the present invention, the method may quantify the expression or concentration of just one of REG1A and REG1B. In alternative embodiments of the invention, the expression or concentration of both REG1A and REG1B may be separately quantified. In a further embodiment of the invention, a quantification method may be used in which REG1A and REG1B cannot be distinguished and hence they may be quantified together.

References to REG1A include NCBI (GenBank) reference sequence transcript NM_002909.4 (GI:189491780), NCBI protein ID NP_002900.2 (GI:29725633), GeneID: 5967 and HGNC:9951. This gene has 4 splice variants (retained introns), but only one is protein coding (166 amino acids).

(SEQ ID NO: 2)
MAQTSSYFMLISCLMFLSQSQGQEAQTELPQARIS

CPEGTNAYRSYCYYFNEDRETWVDADLYCQNMNSG

NLVSVLTQAEGAFVASLIKESGTDDSNVWIGLHDP

KKNRRWHWSSGSLVSYKSWGIGAPSSVNPGYCVSL

TSSTGFQKWKDVPCEDKFSFVCKFKN

References to REG1S include NCBI (GenBank) reference sequence transcript NM_006507.3 (GI:189491779), NCBI protein ID NP 006498.1, GeneID:5968 and HGNC:9952 NCBI. There are 5 splice variants of this gene (retained introns), only two code for the proteins of 166 amino acids and 149 amino acids.

(SEQ ID NO: 3)
MAQTNSFFMLISSLMFLSLSQGQESQTELPNPRIS

CPEGTNAYRSYCYYFNEDPETWVDADLYCQNMNSG

NLVSVLTQAEGAFVASLIKESSTDDSNVWIGLHDP

KKNRRWHWSSGSLVSYKSWDTGSPSSANAGYCASL

TSCSGFKKWKDESCEKKFSFVCKFKN

Note that references to "REG1" herein refer to both REG1A and REG1B, since generally either can be used. However, in some embodiments, both REG1A and REG1B may be used.

TFF1 refers to trefoil factor 1. TFF1 belongs to a family of gastrointestinal secretory peptides, which interact with mucins and are expressed at increased levels during reconstitution and repair of mucosal injury. They protect epithelial cells from apoptotic death and increase their motility, but also play similar pivotal roles in cancer cells, and are thus involved in the development and progression of various cancer types. References to TFF1 include NCBI (GenBank) reference sequence transcript NM_003225.2 (GI: 48928023), NCBI protein NP_003216.1 (GI:4507451), Gene ID:7031 and HGNC:11755.

(SEQ ID NO: 4)
MATMENKVICALVLVSMLALGTLAEAQTETCTVAP

RERQNCGFPGVTPSQCANKGCCFDDTVRGVPWCFY

PNTIDVPPEEECEF

The method of the invention can be performed in a qualitative format, which determines the presence or absence of a cancer marker protein in the sample, but preferably in a quantitative format, which, in addition, provides a measurement of the quantity of cancer marker protein present in the sample. The quantity of marker protein present in the sample may be calculated using any of the above described techniques. In this case, prior to performing the assay, it may be necessary to draw a standard curve by measuring the signal obtained using the same detection reaction that will be used for the assay from a series of standard samples containing known concentrations of the cancer marker protein. The quantity of cancer marker present in a sample to be screened can then extrapolated from the standard curve.

Generally, an increase in one or more of the biomarkers in a test sample compared to a control sample from a healthy patient indicates the presence of chronic pancreatitis and/or PDAC. The threshold concentrations of each of the biomarkers may differ from patient to patient or population to population. Indicative protein concentrations from unprocessed ("raw" or "crude") urine samples are shown below:

|  | Healthy | CP | PDAC |
| --- | --- | --- | --- |
| LYVE1 | ≤2 ng/ml | 2-10 ng/ml | ≥10 ng/ml |
| REG1A | ≤120 ng/ml | 120-500 ng/ml | ≥500 ng/ml |
| REG1B | ≤40 ng/ml | 40-100 ng/ml | ≥100 ng/ml |
| TFF1 | ≤2.5 ng/ml | 2.5-4 ng/ml | ≥4 ng/ml |

For example, if a sample contains between 2 and 10 ng/ml LYVE1, between 120 and 500 ng/ml REG1A, between 40 and 100 ng/ml REG1B and/or between 2.5 to 5 ng/ml TFF1, chronic pancreatitis may be suspected. However, these ranges are indicative, and the skilled person will realise that the concentration of each protein will need to be considered in context, for example depending on the origin of the sample and any pre-processing of that sample that may have taken place. The more of the biomarkers that fall within the relevant concentration thresholds, the more likely it is the patient is healthy, has CP or has PDAC.

For example, if an unprocessed urine sample meets at least one of the following criteria (optionally at least 2, 3 or 4 of the following criteria), chronic pancreatitis may be suspected:
 a) between 2 and 10 ng/ml LYVE1
 b) between 120 and 500 ng/ml REG1A
 c) between 40 and 100 ng/ml REG1B and/or
 d) between 2.5 to 5 ng/ml TFF1

If an unprocessed urine sample meets at least one of the following criteria (optionally at least 2, 3 or 4 of the following criteria), PDAC may be suspected:
 a) more than 10 ng/ml LYVE1
 b) more than 500 ng/ml REG1A
 c) more than 100 ng/ml REG1B and/or
 d) more than 5 ng/ml TFF1

Of course, methods of diagnosis using the biomarker panels of the invention can be further confirmed by, for example, testing a biopsy for the presence of PDAC, and/or the use of additional biomarkers (such as CA19.9).

In one embodiment of the invention, the method may comprise detecting the level of expression or concentration of a protein selected from the group consisting of LYVE1, REG1 and TFF1, or combinations thereof, in a urine sample. In some embodiments of the invention, the method may comprise quantifying the level of expression or concentration of only one of LYVE1, REG1 and TFF1 in a urine sample. In other embodiments of the invention, the method may comprise quantifying the level of expression or concentration of any two of LYVE1, REG1 and TFF1, for example LYVE1 and REG1 (REG1A and/or REG1B), LYVE1 and TFF1, or REG1 (REG1A and/or REG1B) and TFF1. In some embodiments of the invention, the method may comprise detecting the level of expression of all of LYVE1, REG1 (REG1A and/or REG1B) and TFF1. CA19.9 may also be quantified in some embodiments of the invention.

Types of Pancreatic Cancer

The present invention is useful in the diagnosis of PDAC. The PDAC may be early stage PDAC, for example stage I or stage II PDAC, or it may be late-stage PDAC, for example stage III or stage IV PDAC. However, the present invention is particularly useful in detecting early-stage PDAC, in particular stage I to stage IIA PDAC.

In one embodiment of the invention there is thus provided a method of diagnosing or detecting stage I or stage II PDAC, comprising detecting the level of expression or concentration of LYVE1, REG1 (REG1A and/or REG1B) and/or TFF1 in a urine sample and comparing each of the detected expression levels with a reference or references. The methods in particular may determine the presence of stage I and/or stage II PDAC and distinguish these from healthy samples, patients having CP and patients having IPMNs.

Classification of PDAC can be done according to the The American Joint Committee on Cancer (AJCC) tumour-nodes-metastasis (TNM) staging system. The T score describes the size of the main (primary) tumour and whether it has grown outside the pancreas and into nearby organs. The N score describes the spread to nearby (regional) lymph nodes. The M score indicates whether the cancer has metastasized (spread) to other organs of the body:
 Tx, T0, Tis: see TNM system
 T1: tumour <2 cm in greatest dimension, limited to pancreas
 T2: tumour >2 cm in greatest dimension, limited to pancreas
 T3: extension beyond pancreas, no involvement of SMA or coeliac axis
 T4: involvement of SMA or coeliac axis
Regional Lymph Nodes (N)
 Nx: nodes cannot be assessed
 N0: no evidence of nodal involvement
 N1: regional nodal metastases present
Metastases (M)
 Mx: presence of metastases cannot be assessed
 M0: no evidence of metastases
 M1: distant metastases present Stage I PDAC is the earliest stage, where cancer is confined to the pancreas, and there is no cancer in the lymph nodes. In Stage II, the cancer is locally invasive. Cancer in both of these stages is still resectable: currently, fewer than 1 in 5 cancers of the pancreas (<20%) are diagnosed at stage I/II. References to stage II PDAC herein include stage IIA and IIB. In stage cancer has spread beyond pancreas and is in large blood vessels, so unresectable. Stage IV cancer has metastasized to distant sites (and again not treatable by surgery). References herein to detecting or diagnosing PDAC generally refer to detecting or diagnosing each stage PDAC, in particular stage I or stage II PDAC. Such methods are particularly useful given the cancer is still treatable by resection at this stage and survival rates are much improved.

With reference to the TNM score, the stage groupings are:
 stage 0: Tis N0 M0
 stage Ia: T1 N0 M0
 stage Ib: T2 N0 M0
 stage IIa: T3 N0 M0
 stage IIb: T1, T2 or T3 with N1 M0
 stage III: T4 and M0 (any N)
 stage IV: M1 (any T any N)

Biological Samples

The biological sample may be a urine sample, a whole blood sample, a serum sample or a biopsy (such as a pancreatic tissue sample), although urine samples are particularly useful. The method may include a step of obtaining or providing the biological sample, or alternatively the sample may have already been obtained from a patient, for example in ex vivo methods.

Biological samples obtained from a patient can be stored until needed. Suitable storage methods include freezing within two hours of collection. Maintenance at −80° C. can be used for long-term storage.

The sample may be processed prior to determining the level of expression of the gene(s)/protein(s). The sample may be subject to enrichment (for example to increase the concentration of the biomarkers being quantified), centrifugation or dilution. In other embodiments, the samples do not undergo any pre-processing and are used unprocessed.

In some embodiments of the invention, the biological sample may be enriched for the protein biomarkers prior to detection and quantification (i.e. measurement). The step of enrichment can be any suitable pre-processing method step to increase the concentration of protein in the sample. For example, the step of enrichment may comprise centrifugation and/or filtration to remove cells or unwanted analytes from the sample.

The methods of the invention may be carried out on one test sample from a patient. Alternatively, a plurality of test samples may be taken from a patient, for example 2, 3, 4 or 5 samples. Each sample may be subjected to a single assay to quantify one of the biomarker panel members, or alternatively a sample may be tested for all of the biomarkers being quantified.

Methods and Uses of the Invention

The present invention provides a panel of biomarkers useful in the detection of PDAC and, in particular, differentially diagnosing early stage PDAC from late stage PDAC, CP and pancreatitis.

In one embodiment of the invention, the method comprises the steps of:
 a) detecting biomarkers of interest, in particular proteins, in a biological sample obtained from a patient; and
 b) quantifying the expression level or concentration of each of the biomarkers The biomarkers belong to the biomarker panel of the invention. Hence, detection/quantification comprises detection/quantification of one or more of the following biomarkers:
 1) LYVE1
 2) REG1 (REG1A and/or REG1B)
 3) TFF1
 4) CA19.9

In one preferred embodiment, the invention comprises analysis of at least one biomarker selected from the group consisting of LYVE1, REG1 and TFF1, in combination with the biomarker CA19.9.

The level of expression of a gene or protein can be determined in a number of ways. Levels of expression may be determined by, for example, quantifying the biomarkers by determining the concentration of protein in the sample (such as a urine sample). Alternatively, the amount of mRNA in the sample (such as a tissue sample) may be determined. Once the level of expression or concentration has been determined, the level can be compared to a previously measured level of expression or concentration (either in a sample from the same subject but obtained at a different point in time, or in a sample from a different subject, for example a healthy subject, i.e. a control or reference sample) to determine whether the level of expression or protein concentration is higher or lower in the sample being analysed.

In the present invention, an increase in expression (and hence protein concentration) compared to a healthy patient in one or all of LYVE1, REG1 and/or TFF1 is indicative of PDAC or CP. The panel is particularly useful at correctly diagnosing early-stage PDAC. False negatives and false positives can also be minimised try utilising all panel members together. CA19.9 may also be included in the biomarker panel to further reduce the incidence of false positives or false negatives.

Methods for detecting the levels of protein expression include any methods known in the art. For example, protein levels can be measured indirectly using DNA or mRNA arrays. Alternatively, protein levels can be measured directly by measuring the level of protein synthesis or measuring protein concentration.

DNA and mRNA arrays (microarrays) comprise a series of microscopic spots of DNA or RNA oligonucleotides, each with a unique sequence of nucleotides that are able to bind complementary nucleic acid molecules. In this way the oligonucleotides are used as probes to which only the correct target sequence will hybridise under high-stringency condition. In the present invention, the target sequence is either the coding DNA sequence or unique section thereof, corresponding to the protein whose expression is being detected, or the target sequence is the transcribed mRNA sequence, or unique section thereof, corresponding to the protein whose expression is being detected.

Directly measuring protein expression and identifying the proteins being expressed in a given sample can be done by any one of a number of methods known in the art. For example, 2-dimensional polyacrylamide gel electrophoresis (2D-PAGE) has traditionally been the tool of choice to resolve complex protein mixtures and to detect differences in protein expression patterns between normal and diseased tissue. Differentially expressed proteins observed between normal and tumour samples are separate by 2D-PAGE and detected by protein staining and differential pattern analysis. Alternatively, 2-dimensional difference gel electrophoresis (2D-DIGE) can be used, in which different protein samples are labelled with fluorescent dyes prior to 2D electrophoresis. After the electrophoresis has taken place, the gel is scanned with the excitation wavelength of each dye one after the other. This technique is particularly useful in detecting changes in protein abundance, for example when comparing a sample from a healthy subject and a sample form a diseased subject.

Commonly, proteins subjected to electrophoresis are also further characterised by mass spectrometry methods. Such mass spectrometry methods can include matrix-assisted laser desorption/Ionisation time-of-flight (MALDI-TOF).

MALDI-TOF is an ionisation technique that allows the analysis of biomolecules (such as proteins, peptides and sugars), which tend to be fragile and fragment when ionised by more conventional ionisation methods. Ionisation is triggered by a laser beam (for example, a nitrogen laser) and a matrix is used to protect the biomolecule from being destroyed by direct laser beam exposure and to facilitate vaporisation and ionisation. The sample is mixed with the matrix molecule in solution and small amounts of the mixture are deposited on a surface and allowed to dry. The sample and matrix co-crystallise as the solvent evaporates.

Protein microarrays can also be used to directly detect protein expression. These are similar to DNA and mRNA microarrays in that they comprise capture molecules fixed to a solid surface. Capture molecules are most commonly antibodies specific to the proteins being detected, although antigens can be used where antibodies are being detected in serum. Further capture molecules include proteins, aptamers, nucleic acids, receptors and enzymes, which might be preferable if commercial antibodies are not available for the protein being detected. Capture molecules for use on the protein arrays can be externally synthesised, purified and attached to the array. Alternatively, they can be synthesised in-situ and be directly attached to the array. The capture molecules can be synthesised through biosynthesis, cell-free DNA expression or chemical synthesis. In-situ synthesis is possible with the latter two. There is therefore provided a protein microarray comprising capture molecules (such as antibodies) specific for each of the biomarkers being quantified immobilised on a solid support. In one embodiment of the invention, the microarray comprises capture molecules specific for each of LYVE1, REG1 (REG1A and/or REG1B) and TFF1 proteins.

Once captured on a microarray, detection methods can be any of those known in the art. For example, fluorescence detection can be employed. It is safe, sensitive and can have a high resolution. Other detection methods include other optical methods (for example colorimetric analysis, chemiluminescence, label free Surface Plasmon Resonance analysis, microscopy, reflectance etc.), mass spectrometry, electrochemical methods (for example voltametry and amperometry methods) and radio frequency methods (for example multipolar resonance spectroscopy).

Additional methods of determining protein concentration include mass spectrometry and/or liquid chromatography, such as LC-MS, UPLC, or a tandem UPLC-MS/MS system.

Once the level of expression or concentration has been determined, the level can be compared to a previously measured level of expression or concentration (either in a sample from the same subject but obtained at a different point in time, or in a sample from a different subject, for example a healthy subject, i.e. a control or reference sample) to determine whether the level of expression or concentration is higher or lower in the sample being analysed. The methods of the invention may further comprise a step of correlating said detection or quantification with a control or reference to determine if PDAC is present or not. Said correlation step may also detect the presence of particular types of PDAC and to distinguish these patients from healthy patients, in which no PDAC or pancreatic cancer is present, or from patients suffering from CP or intraductal papillary mucinous neoplasms (IPMNs). For example, the methods may detect early stage PDAC, in particular stage I and/or stage II PDAC. Said step of correlation may include comparing the amount of one, two, three, four or more of the panel biomarkers with the amount of the corresponding biomarker(s) in a reference sample, for example in a biological sample taken from a healthy patient. Generally the method does not include the steps of determining the amount of the corresponding biomarker in a reference sample, and instead such values will have been previously determined. However, in some embodiments the methods of the invention may include carrying out the method steps from a healthy patient who is used as a control. Alternatively, the method may use reference data obtained from samples from the same patient at a previous point in time. In this way, the effectiveness of any treatment can be assessed and a prognosis for the patient determined.

Internal controls can be also used, for example quantification of one or more different biomarkers not part of the biomarker panel. This may provide useful information regarding the relative amounts of the biomarkers in the sample, allowing the results to be adjusted for any variances according to different populations or changes introduced according to the method of sample collection, processing or storage.

As would be apparent to a person of skill in the art, any measurements of analyte concentration or expression may need to be normalised to take in account the type of test sample being used and/or and processing of the test sample that has occurred prior to analysis. Data normalisation also assists in identifying biologically relevant results. Invariant biomarkers may be used to determine appropriate processing of the sample. Differential expression calculations may also be conducted between different samples to determine statistical significance.

In general, the methods of the present invention may comprise the steps of:
a) providing a biological sample, such as a urine sample;
b) optionally processing the sample, for example to enrich the sample for miRNAs; and
c) quantification of the biomarkers.
The methods may further comprise the step of:
d) comparison of the level of protein expression from step d) with a control or reference sample.

In some embodiments of the invention, the step of quantification may comprise the following steps:
a) contacting the sample with a binding partner that specifically binds to the biomarker of interest
b) quantifying the amount of biomarker-binding partner to determine the amount of the biomarker present in the original sample.

The present invention therefore provides a reaction mixture, comprising either the protein biomarkers of interest, or a biological sample (such as a urine sample) containing the protein biomarkers of interest, wherein the protein biomarkers of interest are bound to respective binding partners specific to the protein biomarkers. The binding partners may be, for example, antibodies that specifically bind to the protein biomarkers of interest. In one embodiment, the reaction mixture comprises LYVE1, REG1 and TFF1 proteins bound to respective selective binding molecules, such as antibodies. The selective binding molecules are exogenous.

In some embodiments of the invention, the method comprises correlating the measured biomarkers with PDAC, in particular stage I or stage II PDAC. The present invention therefore provides a method of qualifying pancreatic disease in a patient, or determining the presence or absence of pancreatic disease, the method comprising measuring the abundance of one or more relevant biomarkers in a biological sample (such as a urine sample) and correlating the measured biomarkers with a stage of disease. The stage of disease may be chronic pancreatitis, stage I PDAC, or a later stage of PDAC. Alternatively, it may be determined the patient is healthy, i.e. pancreatic disease is absent.

As noted above, the method of the invention can be carried out using an exogenous binding molecules or reagents specific for the protein or proteins being detected. "Exogenous" refers to the fact the binding molecules or reagents have been added to the sample undergoing analysis. Binding molecules and reagents are those molecules that have an affinity for the protein or proteins being detected such that they can form binding molecule/reagent-protein complexes that can be detected using any method known in the art. The binding molecule of the invention can be an antibody, an antibody fragment, a protein or an aptamer or molecularly imprinted polymeric structure. Methods of the invention may comprise contacting the biological sample with an appropriate binding molecule or molecules. Said binding molecules may form part of a kit of the invention, in particular they may form part of the biosensors of in the present invention.

Antibodies can include both monoclonal and polyclonal antibodies and can be produced by any means known in the art. Techniques for producing monoclonal and polyclonal antibodies which bind to a particular protein are now well developed in the art. They are discussed in standard immunology textbooks, for example in Roitt et al., Immunology, second edition (1989), Churchill Livingstone, London. Polyclonal antibodies can be raised by stimulating their production in a suitable animal host (e.g. a mouse, rat, guinea pig, rabbit, sheep, chicken, goat or monkey) when the antigen is injected into the animal. If necessary, an adjuvant may be administered together with the antigen. The antibodies can then be purified by virtue of their binding to antigen or as described further below. Monoclonal antibodies can be produced from hybridomas. These can be formed by fusing myeloma cells and B-lymphocyte cells which produce the desired antibody in order to form an immortal cell line. This is the well-known Kohler & Milstein technique (Kohler &

Milstein (1975) *Nature,* 256:52-55). The antibodies may be human or humanised, or may be from other species.

After the preparation of a suitable antibody, it may be isolated or purified by one of several techniques commonly available (for example, as described in Harlow & Lane eds., Antibodies: A Laboratory Manual (1988) Cold Spring Harbor Laboratory Press). Generally, suitable techniques include peptide or protein affinity columns, high performance liquid chromatography (HPLC) or reverse phase HPLC (RP-HPLC), purification on Protein A or Protein G columns, or combinations of these techniques. Recombinant and chimeric antibodies can be prepared according to standard methods, and assayed for specificity using procedures generally available, including ELISA, ABC, dot-blot assays.

The present invention includes antibody derivatives which are capable of binding to antigen. Thus the present invention includes antibody fragments and synthetic constructs. Examples of antibody fragments and synthetic constructs are given in Dougall et al. (1994) *Trends Biotechnol,* 12:372-379.

Antibody fragments or derivatives, such as Fab, F(ab')$_2$ or Fv may be used, as may single-chain antibodies (scAb) such as described by Huston et al. (993) *Int Rev Immunol,* 10:195-217, domain antibodies (dAbs), for example a single domain antibody, or antibody-like single domain antigen-binding receptors. In addition antibody fragments and immunoglobulin-like molecules, peptidomimetics or non-peptide mimetics can be designed to mimic the binding activity of antibodies. Fv fragments can be modified to produce a synthetic construct known as a single chain Fv (scFv) molecule. This includes a peptide linker covalently joining VH and VL regions which contribute to the stability of the molecule. The present invention therefore also extends to single chain antibodies or scAbs.

Other synthetic constructs include CDR peptides. These are synthetic peptides comprising antigen binding determinants. These molecules are usually conformationally restricted organic rings which mimic the structure of a CDR loop and which include antigen-interactive side chains. Synthetic constructs also include chimeric molecules. Thus, for example, humanised (or primatised) antibodies or derivatives thereof are within the scope of the present invention. An example of a humanised antibody is an antibody having human framework regions, but rodent hypervariable regions. Synthetic constructs also include molecules comprising a covalently linked moiety which provides the molecule with some desirable property in addition to antigen binding. For example the moiety may be a label (e.g. a detectable label, such as a fluorescent or radioactive label) or a pharmaceutically active agent.

In those embodiments of the invention in which the binding molecule is an antibody or antibody fragment, the method of the invention can be performed using any immunological technique known in the art. For example, ELISA, radio immunoassays or similar techniques may be utilised. In general, an appropriate autoantibody is immobilised on a solid surface and the sample to be tested is brought into contact with the autoantibody. If the cancer marker protein recognised by the autoantibody is present in the sample, an antibody-marker complex is formed. The complex can then be directed or quantitatively measured using, for example, a labelled secondary antibody which specifically recognises an epitope of the marker protein. The secondary antibody may be labelled with biochemical markers such as, for example, horseradish peroxidase (HRP) or alkaline phosphatase (AP), and detection of the complex can be achieved by the addition of a substrate for the enzyme which generates a colorimetric, chemiluminescent or fluorescent product. Alternatively, the presence of the complex may be determined by addition of a marker protein labelled with a detectable label, for example an appropriate enzyme. In this case, the amount of enzymatic activity measured is inversely proportional to the quantity of complex formed and a negative control is needed as a reference to determining the presence of antigen in the sample. Another method for detecting the complex may utilise antibodies or antigens that have been labelled with radioisotopes followed by a measure of radioactivity. Examples of radioactive labels for antigens include $^3$H, $^{14}$C and $^{125}$I.

Aptamers are oligonucleotides or peptide molecules that bind a specific target molecule. Oligonucleotide aptamers include DNA aptamer and RNA aptamers. Aptamers can be created by an in vitro selection process from pools of random sequence oligonucleotides or peptides. Aptamers can be optionally combined with ribozymes to self-cleave in the presence of their target molecule.

Aptamers can be made by any process known in the art. For example, a process through which aptamers may be identified is systematic evolution of ligands by exponential enrichment (SELEX). This involves repetitively reducing the complexity of a library of molecules by partitioning on the basis of selective binding to the target molecule, followed by re-amplification. A library of potential aptamers is incubated with the target protein before the unbound members are partitioned from the bound members. The bound members are recovered and amplified (for example, by polymerase chain reaction) in order to produce a library of reduced complexity (an enriched pool). The enriched pool is used to initiate a second cycle of SELEX. The binding of subsequent enriched pools to the target protein is monitored cycle by cycle. An enriched pool is cloned once it is judged that the proportion of binding molecules has risen to an adequate level. The binding molecules are then analysed individually. SELEX is reviewed in Fitzwater & Polisky (1996) *Methods Enzymol,* 267:275-301.

Thus, in one embodiment of the invention, there is provided a method of diagnosing PDAC or CP comprising contacting a biological sample (such as a urine sample) from a patient with reagents or binding molecules specific for the biomarker proteins being quantified, and measuring the abundance of protein-reagent or protein-binding molecule complexes, and correlating the abundance of protein-reagent or protein-binding molecule complexes with the concentration of the relevant protein in the biological sample. For example, in one embodiments of the invention, the method comprises the steps of:

a) contacting a biological sample (such as a urine sample) with reagents or binding molecules specific for one or more of LYVE1, REG1 (REG1A and/or REG1B) and TFF1;

b) quantifying the abundance of protein-reagent or protein-binding molecule complexes for one or more of LYVE1, REG1 (REG1A and/or REG1B) and TFF1; and c) correlating the abundance of protein-reagent or protein-binding molecule complexes with the concentration of one or more of the proteins LYVE1, REG1 (REG1A and/or REG1S) and TFF1 in the biological sample.

The method may further comprise the step of d) comparing the concentration of the proteins in step c) with a reference to determine the presence or absence of PDAC or CP. The patient can then be treated accordingly. In some embodiments of the invention, the methods comprise contacting the biological sample with reagents or binding molecules specific for one, two or three of LYVE1, REG1 (REG1A and/or REG1B) and TFF1, and, in some embodiments, all of the panel biomarkers. In further embodiments, CA19.9 may be included by additionally contacting the biological sample with a reagent or binding molecule specific for CA19.9. Suitable reagents or binding molecules may include an antibody or antibody fragment, an enzyme, a nucleic acid, an organelle, a cell, a biological tissue, imprinted molecule or a small molecule. Such methods may be carried out using kits or biosensors of the invention.

The present invention also provides a method of diagnosis for pancreatic ductal adenocarcinoma comprising detecting the level of expression or concentration of a protein selected from the group consisting of LYVE1, REG1 (REG1A and/or REG1B) and TFF1, or combinations thereof, in a biological sample, in particular a urine sample. In one embodiment of the invention, the method may comprise detecting the level of expression of two proteins selected from the group consisting of LYVE1, REG1 (REG1A and/or REG1B) and TFF1, in a biological sample, in particular a urine sample. In some embodiments of the invention, the method may comprise detecting the level of expression of LYVE1, TFF1 and either or both of REG1A and REG1B in a biological sample, in particular a urine. Since the biomarker panel of the invention can also detect chronic pancreatitis, analogous methods of diagnosis of CP are also provided.

The presence of pancreatic ductal adenocarcinoma can be determined by detecting an increase in gene expression or protein concentration as compared with the level of expression or protein concentration of the corresponding genes or proteins in samples taken from healthy control subjects. In addition, the level of expression or concentration can be used to distinguish between PDAC and CP. This can be achieved by comparing the level of expression or concentration found in the test sample with that seen in patients presenting with CP (or to a reference). Furthermore, the biomarkers can be used to distinguish between PDAC and intraductal papillary mucinous tumours (IPMNs), This can be done by comparing the level of expression or concentration found in the test sample with that seen in patients presenting with IPMNs (or to a reference).

In a further embodiment of the invention there is provided a protein selected from the group consisting of LYVE1, REG1 (REG1A and/or REG1B) and TFF1, or a combination thereof, for use in diagnosing pancreatic ductal adenocarcinoma (PDAC) or CP. In one embodiment of the invention, there is provided the combination of two of LYVE1, REG1 and TFF1 for use in the diagnosis of PDAC or CP (for example LYVE1 and REG1 (REG1A and/or REG1B), LYVE1 and TFF1, or REG1 (REG1A and/or REG1B) and TFF1). In another embodiment of the invention, there is the provided the combination of three of LYVE1, REG1 (REG1A and/or REG1B) and TFF1 for use in the diagnosis of PDAC or CP. There is also provided the combination of all four of LYVE1, REG1A, REG1B and TFF1 for use in the diagnosis of PDAC or CP. These biomarker panels may additionally be combined with CA19.9 in some embodiments of the present invention.

In another embodiment of the invention there is provided a method of treating or preventing PDAC in a patient, comprising quantifying one or more biomarkers selected from the group consisting of LYVE1, REG1 (REG1A and/or REG1B) and TFF1 in a biological sample (in particular a urine sample) obtained from a patient, comparing the values to a reference for each of the quantified biomarkers, and, if the detected values are greater than the reference (or if PDAC is diagnosed or suspected), administering treatment for PDAC. Methods of treating PDAC may include resecting the pancreatic tumour and/or administering chemotherapy and/or radiotherapy to the patient. The biomarkers may be quantified by determining the level of gene expression (for example determining the mRNA concentration) or by determining the protein concentration. In some embodiments, each of LYVE1, REG1 (REG1A and/or REG1B) and TFF1 are quantified. CA19.9 may also be quantified in such methods.

The methods of treating PDAC of the present invention are particularly useful in the treatment of early-stage PDAC. The methods of preventing PDAC are particularly useful in the prevention of late-stage PDAC. In some embodiments, the methods of treatment are performed on patients who have been identified as having a particular concentration of the biomarker proteins in a biological sample. Said concentration is one that it is indicative of PDAC. Accordingly, a method of treating PDAC or CP is provided, comprising resecting any pancreatic tumour and/or administering chemotherapy and/or radiotherapy in a patient in whom PDAC or CP has been diagnosed using a method of the present invention.

In a still further embodiment of the invention there is provided a method for determining the suitability of a patient for treatment for PDAC or CP, comprising detecting the level of expression of a protein selected from the group consisting of LYVE1, REG1 (REG1A and/or REG1B) and TFF1, or combinations thereof, in a urine sample, comparing the level of expression with a control, and deciding whether or not to proceed with treatment for PDAC or CP if PDAC or CP is diagnosed or suspected.

In some embodiments of the invention, the methods may further comprise treating a patient for PDAC or CP if PDAC or CP is detected or suspected. If PDAC or CP is detected or suspect based on the analysis of a urine, blood or serum sample, the presence of PDAC or CP can be confirmed by, for example, detecting the presence and/or amount of the biomarkers in a sample of pancreatic tissue. Methods of the invention may therefore further comprise a step of detecting or determining the amount of a biomarker in a pancreatic tissue sample. The pancreatic tissue sample may have been obtained previously from a patient, or the method may comprise a step of obtaining or providing said pancreatic tissue sample. Analysis of pancreatic tissue samples may also comprise a histological analysis.

If possible, treatment for PDAC (in particular stage I and stage II PDAC) involves resecting the tumour. Treatment may alternatively or additional involve treatment by chemotherapy and/or radiotherapy. Treatment by chemotherapy may include administration of gemcitabine and/or Folfirinox. Folfirinox is a combination of fluorouracil (5-FU), irinotecan, oxaliplatin and folinic acid (leucovorin). Treatment regimens involving Folfirinox may comprise administration of oxaliplatin, followed by folinic acid, followed by irinotecan (alternatively irinotecan may be administered at the same time as folinic acid), followed by 5-FU.

There is also provided a method of monitoring a patient's response to therapy, comprising determining the level of expression of at least one of the biomarkers of interest in a biological sample obtained from a patient that has previously received therapy PDAC (for example chemotherapy and/or radiotherapy). In some embodiments, the level of expression is compared with the level of expression for the same biomarker or biomarkers in a sample obtained from a patient before receiving the therapy. A decision can then be made on whether to continue the therapy or to try an alternative therapy based on the comparison of the levels of expression.

In one embodiment, there is therefore provided a method comprising:
a) determining the level of expression of at least one biomarker of interest, or combination thereof, in a biological sample obtained from a patient that has previously received therapy for pancreatic cancer or PDAC;
b) comparing the level of expression of the biomarker or biomarkers determined in step a) with a previously determined level of expression of the same biomarker or biomarkers (i.e. determined prior to the treatment for pancreatic cancer or PDAC); and
c) maintaining, changing or withdrawing the therapy for pancreatic cancer or PDAC.

The method may comprise a prior step of administering the therapy for pancreatic cancer or PDAC to the patient. In another embodiment, the method may also comprise a pre-step of determining the level of expression of at least one biomarker of interest, or combination thereof, in a biological sample obtained from the same patient prior to administration of the therapy. In step c), the therapy for pancreatic cancer or PDAC may be maintained if an appropriate adjustment in the level(s) of expression of the biomarker or biomarkers is determined. For example, if there is a reduction in the expression of one or more of the biomarkers found to be up-regulated in pancreatic cancer or PDAC, then treatment may be maintained. If the levels of expression have altered sufficiently, for example back to what may be considered healthy or low-risk levels, then treatment for pancreatic cancer or PDAC may be withdrawn. If the levels of expression are unchanged or have worsened (for example there is an increase in the expression of one or more of the biomarkers found to be up-regulated in pancreatic cancer or PDAC), this may be indicative of a worsening of the patient's condition, and hence an alternative therapy for pancreatic cancer or PDAC may be attempted. In this way, drug candidates useful in the treatment of pancreatic cancer or PDAC (in particular early stage PDAC) can be screened.

In another embodiment of the invention, there is provided a method identifying a drug useful for the treatment of PDAC, comprising:
(a) quantifying the expression or concentration of one or more proteins selected from the group consisting of LYVE1, REG1 and TFF1 in a biological sample obtained from a patient;
(b) administering a candidate drug to the patient;
(c) quantifying the expression or concentration of one or more proteins selected from the group consisting of LYVE1, REG1 and TFF1 in a biological sample obtained from the same patient at a point in time after administration of the candidate drug; and
(d) comparing the value determined in step (a) with the value determined in step (c), wherein a decrease in the level of expression or concentration of one or more of the proteins between the two samples identifies the drug candidate as a possible treatment for PDAC. In some embodiments, the method uses all of the panel biomarkers proteins, I.e. all of LYVE1, REG1 and TFF1 must be quantified in step (a) and step (c). In some embodiments, the biological sample is a urine sample. In some embodiments, the drug is a compound, an antibody or antibody fragment.

Kits and Biosensors

In a still further embodiment of the invention there is provided a kit of parts for testing for pancreatic ductal adenocarcinoma comprising a means for quantifying the expression or concentration of LYVE1, REG1 (REG1A and/or REG1B) or TFF1, or combinations thereof. The means may be any suitable detection means.

For example, the means may be a biosensor. In some embodiments, the means may comprise a dipstick coated with a membrane that is bound to an unlabeled binding molecule (such as an antibody or antibody fragment) with specific affinity for the protein being detected on a first section. The membrane may also have a section that is blocked with a non-reactive protein to prevent any molecules binding to that part of the membrane. The membrane may also have a section to which is bound the protein that is being detected in the sample. The dipstick may be equipped to detect more than one protein in a single assay by having different sections dedicated to the detection of different proteins of the invention, such that each further protein to be detected has a corresponding antibody capable of specifically binding that further protein bound on one section of the dipstick, and optionally the further protein to be detected bound on another section of the dipstick. The kit may also comprise a container for the sample or samples and/or a solvent for extracting the biomarkers from the biological sample. The kit may also comprise instructions for use.

In some embodiments of the invention, there is provided a kit of parts for diagnosing pancreatic ductal adenocarcinoma or CP comprising a means for detecting the expression or concentration of at least two of LYVE1, REG1 and TFF1. In further embodiments of the invention, there is provided a kit of parts for diagnosing pancreatic ductal adenocarcinoma or CP comprising a means for detecting the expression or concentration of all three of LYVE1, REG1 and TFF1. The means for detecting the biomarkers may be reagents that specifically bind to or react with the biomarkers being quantified.

The kit of parts of the invention may be a biosensor. A biosensor incorporates a biological sensing element and provides information on a biological sample, for example the presence (or absence) or concentration of an analyte. Specifically, they combine a biorecognition component (a bioreceptor) with a physiochemical detector for detection and/or quantification of an analyte (such as a protein).

The bioreceptor specifically interacts with or binds to the analyte of interest and may be, for example, an antibody or antibody fragment, an enzyme, a nucleic acid, an organelle, a cell, a biological tissue, imprinted molecule or a small molecule. The bioreceptor may be immobilised on a support, for example a metal, glass or polymer support, or a 3-dimensional lattice support, such as a hydrogel support.

Biosensors are often classified according to the type of biotransducer present. For example, the biosensor may be an electrochemical (such as a potentiometric), electronic, piezoelectric, gravimetric, pyroelectric biosensor or ion channel switch biosensor. The transducer translates the interaction between the analyte of interest and the bioreceptor into a quantifiable signal such that the amount of analyte present can be determined accurately. Optical biosensors may rely on the surface plasmon resonance resulting from the interaction between the bioreceptor and the analyte of interest. The SPR can hence be used to quantify the amount of analyte in a test sample. Other types of biosensor include evanescent wave biosensors, nanobiosensors and biological biosensors (for example enzymatic, nucleic acid (such as DNA), antibody, epigenetic, organelle, cell, tissue or microbial biosensors).

Dipsticks are another example of biosensor. The dipsticks of the invention may comprise a membrane. The dipsticks may further comprise a first section to which is bound an unlabeled antibody with specific affinity for the protein whose expression is being detected, a second section that is blocked with a non-reactive protein and a third section to which is bound the protein whose expression is being detected.

Dipstick techniques known in the art can be used to quickly and effectively carry out the method of the invention. Dipstick techniques include the following. A labelled antibody, for example labelled with formazan, having a specific affinity for the protein (antigen) being detected is dissolved in a sample of test fluid. A dipstick on which a nitrocellulose membrane is mounted is immersed in the reaction mixture. The membrane has one section on which non-labelled antibodies having a specific affinity for that antigen are bound. The second section is free of antibodies and is blocked with a non-reactive protein to prevent binding of labelled antibodies to the membrane. A third section of the dipstick is provided on which the antigen is bound. Reactions take place between the free antigen in the test fluid and the non-labelled antibody bonded to the membrane, as well as between the free antigen and the labelled antibody that was added to the sample. This results in a sandwich of non-labelled bonded antibody/antigen/labelled antibody over the first section of the membrane. A reaction also takes place between the labelled antibody and the bound antigen over the third section. No reaction takes places over the second section of the membrane.

The reaction is allowed to proceed for a fixed period of time or until completion is determined visually. Since formazan is a highly coloured dye, the reacted formazan-labelled antibody imparts colour to the third section, and if the antigen is present in the test fluid, to the first section as well. Since no reaction takes place over the second section, no colour is developed over that section. The second section thus acts as a negative control. In cases in which colour is imparted across the entire membrane, including the second section due to absorption of un-reacted formazan particles and, to a minor extent, of un-reacted formazan-labelled antibody, presence of the antigen is indicated by a difference in colour between the first and second sections of the membrane. The third section is provided as a positive control by demonstrating that the appropriate reactions are in fact taking place.

The length of time that the dipstick is immersed in the mixture is that which allows a difference in colour intensity to develop between the first and second sections of the membrane if the antigen is present. For most antibody-antigen reactions, colour development is essentially complete within 30 to 60 minutes. If desired, colour development of the dipstick can be monitored by simply removing the dipstick, visually checking the colour intensity across the first section of the membrane, and then re-immersing the dipstick if required. When no further change in colour intensity is seen, the reaction can be deemed complete.

The dipstick can be prepared by any conventional methods known in the art. For example, a nitrocellulose membrane is mounted at the lower end of the dipstick. A solution containing non-labelled primary antibody is applied over one section of the membrane to bind primary antibodies to the membrane. A solution containing a blocking agent (for example 1% serum albumin) is applied over another section of the membrane to prevent subsequent bonding of the primary protein to the membrane.

Dipsticks can be equipped for the detection of more than one protein at a time by including further sections to which are bound un-labelled antibodies with specific affinity for the further protein or proteins being detected and, optionally, a section to which is bound the protein being detected. In such cases, labelled antibodies with specific affinity for the protein being detected can be added to the sample such that their binding to the further section of the dipstick, and hence their presence in the sample, be detected. The antibodies can be labelled with the same dye or with a different dye. Suitable dyes, other than formazan, include acid dyes (for example anthraquinone or triphenylmethane), azo dyes (for example methyl orange or disperse orange 1), fluorescent dyes (for example fluorescein or rhodamine) or any other suitable dye known in the art such as coomassie blue, amido black, toluidine blue, fast green, Indian ink, silver nitrate and silver lactate. It is also apparent that the pre-labelled primary protein reactant is not limited to antibodies, but can include any protein or other molecule having specific affinity for a second protein to be detected in a sample.

The invention also provides protein microarrays (also known as protein chips) comprising capture molecules (such as antibodies) specific for each of the biomarkers being quantified, wherein the capture molecules are immobilised on a solid support. The solid support may be a slide, a membrane, a bead or microtitre plate. The slide may be a glass slide. The membrane may be a nitrocellulose membrane. The array may be a quantitative multiplex ELISA array. The microarrays are useful in the methods of the invention.

In particular, the present invention provides a combination of binding molecules, wherein the each binding molecule specifically binds a different target analyte, and the combination of analytes the binding molecules specifically bind to LYVE1, REG1 or TFF1, or combinations thereof, and optionally CA19.9.

The binding molecules may be present on a solid substrate, such an array. The binding molecules may all be present on the same solid substrate. Alternatively, the binding molecules may be present on different substrates. In some embodiments of the invention, the binding molecules are present in solution.

These kits may further comprise additional components, such as a buffer solution. Other components may include a probe or labelling molecule for the detection of the bound protein and so the necessary reagents (i.e. enzyme, buffer, etc) to perform the labelling; binding buffer; washing solution to remove all the unbound or non-specifically bound miRNAs. Binding of the binding molecules to the target analyte may occur under standard or experimentally determined conditions. The skilled person would appreciate what stringent conditions are required, depending on the biomarkers being measured. The stringent conditions may include a temperature high enough to reduce non-specific binding.

The protein arrays used may use fluorescence labelling to determine the presence and/or concentration of the biomarkers being analysed, although other labels can be used (affinity, photochemical or radioisotope tags). Label-free detection methods can also be used, such as surface plasma resonance (SRR), carbon nanotubes carbon nanowire sensors and microelectromechanical (MEMS) cantilevers. Near-IR fluorescent detection may be particularly useful for quantitative detection, in particular using nitrocellulose coated glass slides.

Quantitative protein analysis using antibody arrays may comprise signal amplification, multicolour detection, and competitive displacement techniques. Other techniques include scanning electron microscopy for the analysis of protein chips (SEMPC), which involves counting target-coated gold particles that interact specifically with ligands or proteins arrayed on a glass slide by utilizing backscattering electron detection. Accordingly, methods of the invention may comprise counting interactions between biomarker protein and their respective specific bindings molecules to achieve a quantitative analysis of the test sample. Quantitative protein detection and analysis is discussed further in, for example, Barry & Solovier, "Quantitative protein profiling using antibody arrays", *Proteomics*, 2004, 4(12):3717-3726.

In one embodiment of the invention, there is provided a method of diagnosing early-stage pancreatic ductal adenocarcinoma (PDAC) comprising determining the concentration of each of LYVE1, REG1 and TFF1 protein in a urine sample and comparing the so determined values to a reference. If the concentration of each of the proteins is greater than the reference value, early-stage PDAC may be present, and the patient can be treated accordingly.

Features for the second and subsequent aspects of the invention are as for the first aspect of the invention mutatis mutandis.

The present invention shall now be further described with reference to the following examples, which are present for the purposes of illustration only and are not to be construed as being limiting on the invention.

EXAMPLES

Clinical Specimens

Healthy, CP and PDAC urine specimens were obtained from the Royal London Hospital (RLH) for the discovery phase (n=18) and from RLH and University College London (later on jointly referred to as "LON"), the Department of Surgery, Liverpool University ("LIV"), and the CNIO Madrid, Spain ("SPA"), (in total 371 urines) for validation purposes. Urine samples for patients with other benign and malignant hepatobiliary pathologies (n=117) were obtained from LIV. All samples were collected with full ethical approval from the involved centres, and with informed consent from all individuals who donated urine samples. The specimens in all participating centres were collected using the same standard operating procedures: clean-catch, midstream urine was collected, frozen within 2 hours of collection and stored at −80° C. until utilized. Of importance, all the samples were derived from patients with no history of renal diseases; dipstick test analysis (Bayer multistix SG 08935414) was also performed to exclude potential bilirubinemia, proteinuria, bacterial contamination and hematuria. Samples were collected before surgery or chemotherapeutic treatment. Matching plasma samples to measure CA19.9 were available from RLH and LIV.

GeLC-MS/MS Analysis of Urine Proteomes

Six urine samples (three males and three females) for each group (H, CP and PDAC; in total 18 samples) were utilised: H males/females age 45, 50, 60/44, 45.54 years; CP maces/females age 46, 48, 51/47, 69.74 years; PDAC males/females age 44, 74, 84/71, 73.77 years; male PDAC stage all IIB/female two 1B, one IIA. All urine samples were desalted and concentrated as described previously (Weeks M E et al. "Analysis of the urine proteome in patients with pancreatic ductal adenocarcinoma", *Proteomics Clinical Applications* 2008; 2:1047-57). 20 µg of each pre-processed pool of three samples per group were separated in duplicate on 4-12% mini-gels (Invitrogen); female and male urines were analysed separately. The gels were stained with Colloidal Coomassie, and each sample lane cut using a grid into 40 equally sized slices. Gel slices were digested robotically with trypsin and resultant peptides analyzed by nano LC/MS/MS using a nanoAcquity (Waters) interfaced to a LTQ Orbitrap XL tandem mass spectrometer (ThermoFisher). Product ion data were searched against the human IPI protein database using Mascot, and subsequently parsed into the Scaffold software (Proteome Software) for collation into non-redundant protein lists. Reversed database searching was used to assess false discovery rates, the target protein FDR being <0.5% per sample. A semi-quantitative assessment of relative protein abundance between PDAC, CP and Healthy samples was obtained by using the spectral counting approach (Liu H et al., "A model for random sampling and estimation of relative protein abundance in shotgun proteomics", Analytical Chemistry, 2004; 76:4193-201).

Urine Biomarkers and CA19.9 Measurements

Total protein concentration in urines was determined by Bradford assay (Coomassie Protein Assay Reagent, Pierce). The quantitative determination of human LYVE-1 (Cat #SEB049Hu, Uscn Life Science Inc.) and human TFF1 (Cat #ELH-LYVE1-001, RayBiotech, Inc.) was performed according to the manufacturer's Instructions; human ReG1A levels were initially assessed in our laboratory, and afterwards by BioVendor Analytical Testing Service (BioVendor Laboratomi medicine a.s). Calibration curves were prepared using purified standards for each protein assessed. Curve fitting was accomplished by a four-parameter logistic regression following the manufacturer's instructions. The limits of detection and the coefficient of variation (CV) for each of the ELISA assays were as follows: LYVE-1—8.19 pg/ml, intra-assay CV—9%, inter-assay CV—12%, TFF1—0.037 ng/ml, intra-assay CV—9%, inter-assay CV—12%. REG1A—0.094 ng/ml, intra-assay CV—9%, inter-assay CV 20%; REG1B-3.13 pg/ml, intra-assay CV—3.9%, inter-assay CV—2.7%. Urine creatinine was measured by the Jaffé method using the Roche Cobas 8000 system (Roche Diagnostics, Mannheim, Germany) at the Clinical Biochemistry Laboratory, RLH (London, UK). Levels of Cal 9.9 in plasma and urine were measured at the Clinical Biochemistry Laboratory, RLH using a Roche Modular E170 instrument according to the routine protocols.

Tissue Microarrays and Immunohistochemistry (IHC) The details of the tissue microarray and scoring procedure used in evaluating the expression of the biomarkers was described previously (Ene-Obong A et al., "Activated pancreatic stellate cells sequester CD8+ T cells to reduce their infiltration of the juxtatumoral compartment of pancreatic ductal adenocarcinoma", *Gastroenterology*, 2013; 145:1121-32). IHC was performed with anti-REG1A (Abcam, Rabbit polyclonal, ab47099, 1:100 dilution), anti-TFF1 (Abeam, Rabbit polyclonal, ab50806, 1:100 dilution), and anti-LYVE1 (Acris, Rabbit polyclonal, DP3500PS, 1:100 dilution) antibodies using the Ventana Discovery system, according to standard protocols (sCC1, 1 h incubation).

Statistical Analysis

To identify potential urine biomarkers from the MS data, the statistical analysis was performed on the normalized data (based on the sum of spectral counts/sample) using Arraytrack software (http:edkb.fda.go/webstart/arraytrack) and a t-test. The data were further filtered according to both p values and fold change between any two sample groups.

The concentrations of the selected proteins (LYVE1, REG1A and TFF1) were subsequently explored using ELISA assays, and the obtained results analysed using nonparametric Kruskal-Wallis test followed by Dunn's post test with GrafPadPrism. Correlation between the three biomarkers was assessed using Pearson's correlation coefficient.

Each individual biomarker and the panel were investigated for their ability to discriminate between PDAC patients (all stages, or early stages I-II) and control samples (healthy and CP) using ROC analysis and an hold-out approach. For each comparison, 70% of the subjects in the patient and control datasets were randomly selected for inclusion in the training dataset. Logistic regression was then applied. All protein concentration data were natural log-transformed and mean-centered prior to regression analysis. In individual biomarker analyses, creatinine-normalised data were used to correct for the urine dilution factor; for the panel analysis, the model included the three biomarkers (prior to creatinine normalisation) and was adjusted for creatinine and age (as the median age of PDAC patients was higher than that of healthy and CP individuals, Table 1), i.e. 5-parameter model. Separate models were applied to me training datasets for me comparison of PDAC all stages versus healthy, PDAC stages I-II versus healthy, PDAC all stages versus CP and PDAC stages I-II versus CP. ROC curves were generated for each of the above regression models; the area under the curve (AUC), and the sensitivity (SN) and specificity (SP) at the 'optimal' cut-point for discrimination between groups were obtained. The optimal cut-point corresponded to the point closest to the top-left part of the plot in the ROC plane (coordinates 0,1) with optimal SN and SP according to the following criterion:

$$\min((1-\text{sensitivities})^2+(1-\text{specificities})^2),$$

as calculated by the 'ci.threshold' procedure of the R 'pROC' package (Robin X et al., "pROC: an open-source package for R and S+ to analyse and compare ROC curves", *BMC Bioinformatics*, 2011; 12:77). This approach been showed to have good performance in the estimation of the optimal cut-point of a biomarker.

The rest of the subjects (30%) formed independent datasets which were used for model validation. For the primary analysis (all PDAC versus Healthy), 49 PDAC and 28 healthy samples give more than 90% power to detect a standardized difference of 1.0 (i.e. a difference between PDAC and healthy samples of at least one standard deviation) using a one-sided test.

Validation was performed by classifying each sample in the validation dataset according to the logistic regression model developed based on the training dataset, and comparing this classification with the actual diagnosis, hence deriving a new ROC curve. The optimal cut-points computed for the training sets were used to derive the SN and SP of the validation dataset. Confidence intervals (CI, 95%) for AUCs were derived based on DeLong' asymptotically exact method to evaluate the uncertainty of an AUC (DeLong E R et al., "Comparing the areas under two or more correlated receiver operating characteristic curves: a nonparametric approach", *Biometrics*, 1988; 44:837-45).); SN and SP, 95% CI were derived using non-parametric stratified resampling with the percentile method (2,000 bootstrap replicates) as described by Carpenter J & Bitheil J., "Bootstrap confidence intervals: when, which, what? A practical guide for medical statisticians", *Stat Med,* 2000; 19:1141-64.). AUCs were compared using DeLong's 1-sided test for correlated/paired AUCs).

For exploratory analyses, ROC curves were derived for the comparison of PDAC stage I-IIA versus healthy or CP based on logistic regression modelling using all available samples.

ROC curve analyses were performed in R version 2.13.0 (The R Foundation for Statistical Computing, http://www.r-project.org/foundation) using procedures from the Epi, pROC http://CRAN.R-project.org/package=Epi and ROCR (Sing T et al., "ROCR: visualizing classifier performance in R.", *Bioinformatics,* 2005; 21:3940-1) packages.

Urine Proteomes

An in-depth proteomics analysis by GeLC/MS/MS of 18 urine specimens derived from PDAC, CP and healthy (H) individuals (6 per group, three males, three females) (FIG. 6A) was undertaken. This analysis resulted in the identification of around 1,500 (1,198 in male and 1,061 in female urine) non-redundant proteins. These proteins originated from all cellular compartments and were mapped using PA (Ingenuity pathway analysis, http://www.ingenuity.com/) to a number of cellular functions and diseases, confirming that urine provides a rich source of diverse proteins with respect to their origin and functional roles.

The MS analysis was performed separately on urine samples from male and female subjects. Considerable gender-specific differences were noticed: of 997 proteins identified in healthy urine samples, 398 (40%) were unique to male urines, 118 (12%) were unique to female and 481 (48%) were common to both.

Among around 200 differentially expressed between the three experimental groups (PDAC, CP, H) three proteins commonly deregulated in both males and females: LYVE1, REG1A and TFF1, were selected for further evaluation based on the statistics (p-values, fold change), interrogation of both Pancreatic Expression Database (PED) (http://www-.pancreasexpression.org/) and additional literature search to for previous knowledge on the potential candidates, and also on the availability of commercial ELISA assays. While REG1B in the proteomics data appeared to be slightly better candidate, only REG1A ELISA assay was available commercially at the time. However, when REG1B ELISA became available, a subset of urine samples was tested and similar results were obtained (see later). The presence of the three selected biomarkers as full-size proteins: 35 kDa for LYVE1, 19 kDa for REG1A, and 9 kDa for TFF1 in urine specimens was confirmed by Western blot examination (data not shown).

Biomarker Panel in Detecting PDAC

The selected biomarkers were subsequently assessed using ELISA assays on 371 urine samples collected from three centres: London and Liverpool, U K, and Madrid, Spain. Demographics and clinical characteristics of patients and healthy participants included in the study are shown in Table 1 (overleaf).

TABLE 1

Demographics and clinical characteristics of the healthy and patient cohorts

| | Normal | | | CP | | | PDAC | | | |
|---|---|---|---|---|---|---|---|---|---|---|
| | Cases (n) | Gender | Age range (Median) | Cases (n) | Gender | Age range (Median) | Cases (n) | Gender | Age range (Median) | Stage/n plasma |
| LON | 87 | M = 46<br>F = 41 | 28-87<br>(55) | 45 | M = 32<br>F = 13 | 29-82<br>(53) | 60 | M = 38<br>F = 22 | 29-82<br>(64) | I = 4/4<br>IIA = 1/1 |
| Plasma (CA19.9) | 28 | M = 16<br>F = 12 | 28-67<br>(46) | 19 | M = 14<br>F = 5 | 29-74<br>(54) | 56 | M = 34<br>F = 22 | 29-82<br>(64) | IIB = 13/13<br>III = 33/30<br>IV = 6/5<br>U = 3/3 |
| LIV | 0 | N/A | N/A | 41 | M = 25<br>F = 16 | 29-82<br>(51) | 91 | M = 53<br>F = 38 | 39-83<br>(68) | I = 3/3<br>IIA = 8/8 |
| Plasma (CA19.9) | 0 | N/A | N/A | 31 | M = 17<br>F = 14 | 37-73<br>(51) | 91 | M = 53<br>F = 38 | 39-83<br>(68) | IIB = 42/42<br>III = 38/38<br>IV = 0/0<br>U = 0/0 |
| SPA | 0 | N/A | N/A | 6 | M = 4<br>F = 2 | 54-68<br>(57) | 41 | M = 23<br>F = 18 | 43-94<br>(72) | I = 0/NA<br>II = 0/NA |
| Plasma (CA19.9) | 0 | N/A | N/A | 0 | N/A | N/A | 0 | N/A | N/A | III = 0/NA<br>IV = 0/NA<br>U = 41/NA |
| Total | 87 | M = 46<br>F = 41 | 28-87<br>(55) | 92 | M = 61<br>F = 31 | 29-82<br>(54) | 192 | M = 114<br>F = 78 | 29-94<br>(68) | I = 7/7<br>IIA = 9/9 |
| Plasma (CA19.9) | 28 | M = 16<br>F = 12 | 28-67<br>(46) | 50 | M = 31<br>F = 19 | 29-74<br>(53) | 147 | M = 87<br>F = 60 | 29-83<br>(67) | IIB = 55/55<br>III = 71/68<br>IV = 6/5<br>U = 44/3 |

PDAC stage I-IV Versus Healthy

Figures 1A, 1B:
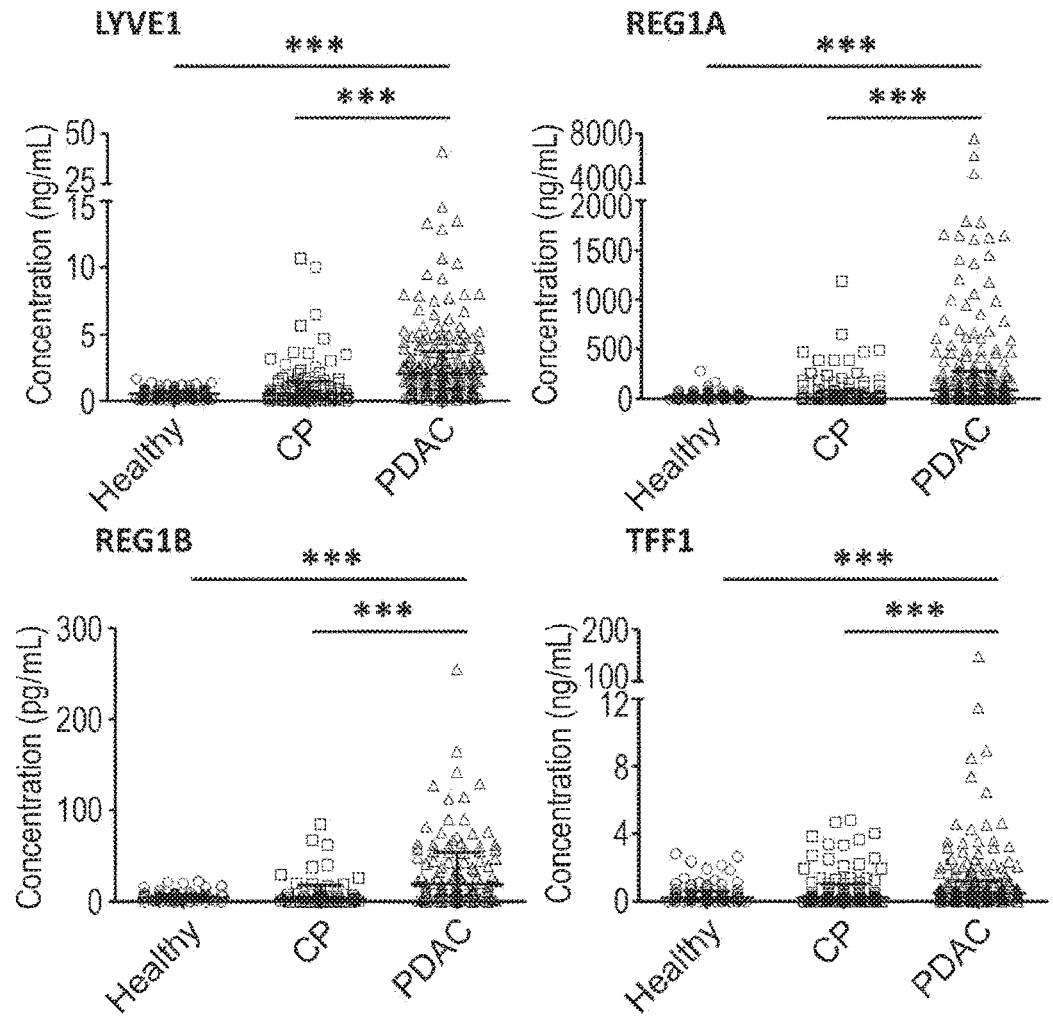
FIG. 1: Urine concentration of the candidate protein biomarkers. A, Scatter dot plots of LYVE1, REG1A, REG1B and TFF1 protein concentration (creatinine-normalised) analyzed by ELISA in healthy, chronic pancreatitis (CP) and pancreatic adenocarcinoma (PDAC) patients' urine. Upper bars: Kruskal-Wallis/Dunn's post test, ***: $P<0.001$; B, Statistical summary, median and Interquartile range (IQR) of raw/creatinine-normalised data for the biomarkers, median and IQR of urine creatinine (mmol/L), as well as plasma CA19.9 by sample groups are shown.

The ELISA analysis showed significantly higher urine concentrations of each of the candidate biomarkers in the urine of PDAC patients (n=192) when compared to healthy samples (n=87, all with p<0.0001, FIG. 1). Of note, REG1B and REG1A ELISA assays produced similar results (FIG. 1).

In PDAC, LYVE1, REG1A and TFF1 were positively correlated with each other, while in healthy samples, only LYVE1 and REG1A were correlated (FIG. 7). The diagnostic performance of LYVE1, REG1A and TFF1 was established using Receiver Operating Characteristic (ROC) curve analysis (FIG. 2). Their individual performance in discriminating between PDAC stage I-IV and healthy urines was assessed first, in a training dataset (70% of the samples, n=143 and n=59, respectively). Individual (creatinine-normalised) urine biomarkers were able to discriminate between the two groups with AUC values of 0.851 (95% CI 0.801-0.902) for LYVE1, 0.823 (95% CI 0.766-0.879) for REG1 and 0.686 (95% CI 0.606-0.765) for TFF1, with respective SN of 76.9% (95% CI 69.3-83.2), 62.2% (95% CI 53.8-69.9) and 72.7% (95% CI 65.0-79.7), and respective SP of 88.1% (95% CI 79.6-96.6), 94.9% (95% CI 88.1-100.0), and 59.3% (95% CI 47.5-71.2) (FIG. 2A, C). The three biomarkers were then combined into a panel adjusted for creatinine and age (FIG. 2B). The results of the logistic regression model underlying the ROC analysis in the training and validation (30% of the samples, PDAC n=49, healthy n=28) datasets are shown in FIGS. 2B and C. The panel achieved SN>75% and SP >85% for AUCs of 0.891 (95% CI 0.847-0.935) and 0.921 (95% CI 0.863-0.978) in the training and validation datasets, respectively, thus showing better performance than any of the individual biomarkers.

PDAC Early Stages Versus Healthy

Figure 3:
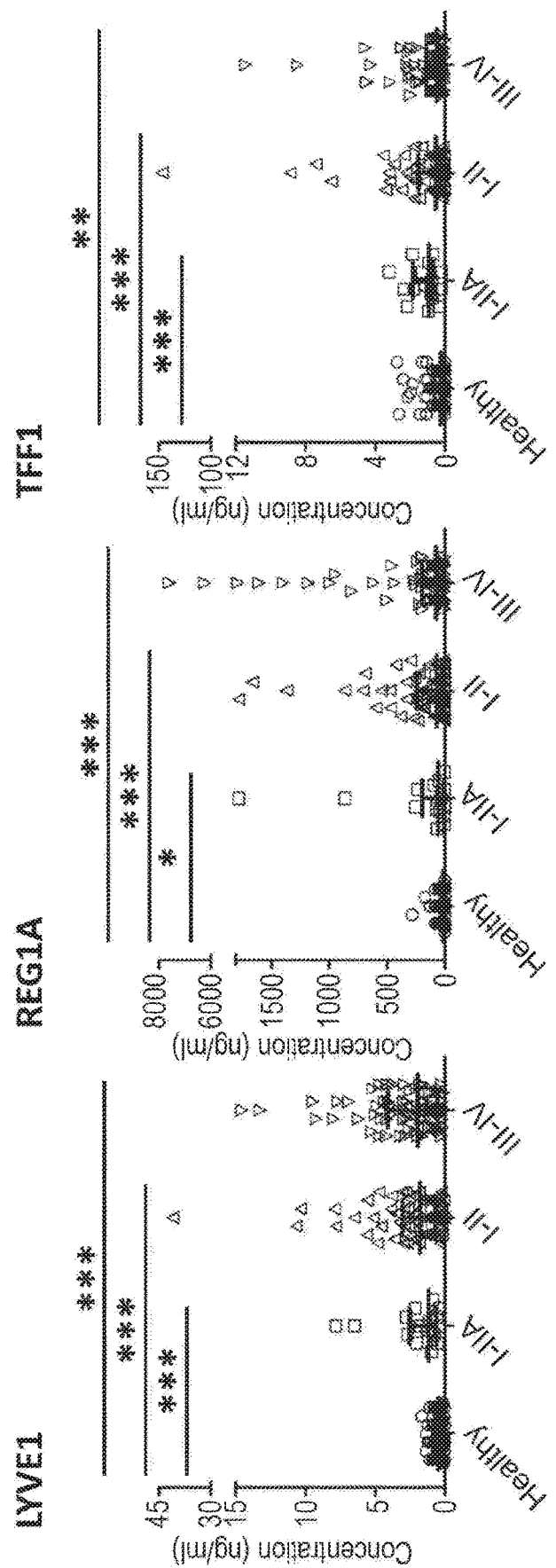
FIG. 3—Urine concentration of the three biomarkers in different stages of pancreatic adenocarcinoma. Scatter dot plots of urine LYVE1, REG1A, TFF1 protein concentration (creatinine-normalised) in urines of healthy (n=87) and pancreatic adenocarcinoma patients at different stages of disease development (I-IIA n=16, I-II n=71, III-IV n=77). Bars indicate median and IQR values. Upper bars: Kruskal-Wallis/Dunn's post test, *: $P<0.05$, : $P<0.01$, *: $P<0.001$.

Next, the performance of the biomarkers in discriminating early stage cancers from healthy individuals was assessed. Tumour staging information was available for 148 (77%) of the PDAC patients. The concentrations of each of the biomarkers were significantly increased in later stages (stage III-IV, n=77, all p<0.001), in stages I-II (n=71, all p<0.001) and in stages I-IIA (locally invasive disease without lymph node metastases, n=16, p<0.05) compared to healthy people (n=87) (FIG. 3). The concentrations of LYVE1 and TFF1 were also higher in stage I cancers (p<0.001 and p<0.05, respectively; data not shown). As a limited number of stage I urine samples was available (n=7), the diagnostic accuracy of the urine markers on combined PDAC stage I-II data was assessed. The performance of the individual markers and the panel in discriminating between PDAC stage I-II from healthy urines was first assessed in a new training dataset (70% of the samples; PDAC stage I-II n=56 and healthy n=61, respectively). A new 5-parameter model was built using this training dataset and validated using the rest of the data (30% of the samples; PDAC stage I-II n=15, Healthy n=26) (FIG. 4A, B). The panel achieved AUCs of 0.900 (95% CI 0.843-0.957) and 0.928 (95% CI 0.843-1.000) in the training and validation datasets, respectively (FIG. 4C). Therefore, the urine biomarker panel can differentiate early PDAC from healthy samples with high accuracy.

As an exploratory analysis, the urine samples from individuals for which matched plasma samples were available were selected so CA19.9 values could be obtained. The ROC curves were derived for plasma CA19.9 (as a categorical variable with a cut-off at clinically established threshold of 37 U/mL), the panel, and a combination of the panel and CA19.9. For the comparison of PDAC stage I-II (n=71)

versus healthy (n=28) samples, AUCs of 0.880 (95% CI 0.947-0.999) for CA19.9, and 0.973 (95% CI 0.947-0.999) were obtained for the panel, which was significantly greater than plasma CA19.9 alone (p=0.005). The addition of plasma CA19.9 to the panel significantly increased the AUC to 0.991 (95% CI 0.979-1.000, p=0.04, FIG. 5A/C). When PDAC stage I-IIA (n=16) were compared to healthy samples, AUCs were 0.839 (95% CI 0.719-0.959) for CA19.9, and 0.971 (95% CI 0.929-1.000) for the panel (p=0.006). The addition of plasma CA19.9 to the panel did not result in any improvement (AUC=0.969, 95% CI 0.924-1.000, p=0.7, FIG. 5B/C).

Biomarker Panel in Differentiating PDAC from CP

The ability of the biomarker panel in differentiating PDAC from CP was assessed.

PDAC Stage I-IV Versus CP

Urine concentration for all three biomarkers was higher in PDAC (n=192) compared to CP samples (n=92), all with p<0.001, (FIG. 1) and as for PDAC, the biomarker concentrations were positively correlated with each other in the CP data (FIG. 7). In the training dataset (PDAC n=143, CP n=62) LYVE1 and REG1 were able to discriminate between the two groups with SN of 77-78% and SP of 66-69% (respective AUC values of 0.775 (95% CI 0.704-0.846) and 0.722 (95% CI 0.643-0.801, FIG. 8), while the SP of TFF1 only reached 50% for a similar SN. Combining the three biomarkers into a panel only improved marginally the performance of LYVE1 and REG1 alone as assessed in the training (AUC=0.815, 95% CI 0.752-0.878), and validation (PDAC n=49, CP n=30, AUC=0.839, 95% CI 0.751-0.928) datasets.

PDAC Early Stages Versus CP

Biomarker urine concentrations were significantly increased in stages I-II PDAC (n=71) compared to CP (n=87), with p<0.001 for each of the three biomarkers (data not shown). The panel achieved high SN (>85%) in both the training (PDAC stage I-II n=56, CP n=66) and validation (PDAC stage I-II n=15, CP n=26) datasets, but relatively low SP (66.7% and 50%), similar to the SP observed for individual biomarkers, with respective AUCs of 0.831 (95% CI 0.762-0.901) and 0.846 (95% CI 0.730-0.963, FIGS. 8D-F).

As before, the panel was explored in combination with plasma CA19.9. For the comparison of PDAC stage I-II (n=71) versus CP (n=50) samples, the ROC curves showed AUCs of 0.775 (95% CI 0.699-0.852) for CA19.9, 0.830 (95% CI 0.759-0.902) for the panel (p=0.1), and 0.885 (95% CI 0.825-0.945) for the panel in combination with CA19.9 (p=0.01 for superiority over the panel alone) (FIGS. 9A/C). In the comparison of PDAC stage I-IIA (n=16) versus CP, the ROC curves showed AUCs of 0.735 (95% CI 0.609-0.861) for CA19.9, 0.871 (95% CI 0.770-0.972) for the panel (p=0.004 for superiority over plasma CA19.9), and 0.866 (95% CI 0.749-0.984) for the combination (p=0.6) (FIG. 9B/C). Therefore, the panel performed better in differentiating stage I-IIA from CP than CA19.9.

Biomarker Expression in Urine of Other Hepatobiliary Pathologies

Finally, the expression of the biomarkers in urine specimens collected from patients with several other benign or malignant hepatobiliary pathologies was explored and compared to the expression in patients with early stage PDAC (FIG. 10). Urine levels of LYVE1 in PDAC stage I-II samples were higher than in IPMNs, AMP and pancreatic NETs specimens; REG1A levels were only significantly higher in early stage PDAC compared to IPMNs. Plasma CA19.9 levels were significantly higher in PDACs stage I-II compared to pancreatic NETs and DuCA samples. This might suggest a potential utility for LYVE1 and REG1A in distinguishing other benign or malignant hepatobiliary pathologies from early stage PDACs.

Tissue Origin of the Three Biomarkers

Having demonstrated a good performance of the panel in differentiating early cancer patients from healthy individuals, it was next sought to establish the expression of the biomarkers in pancreatic tissue. Immunohistochemistry (IHC) was performed using in-house constructed PDAC tissue microarrays. A strong expression of REG1A was seen in histologically normal adjacent acinar cells, but the staining was also seen in 44/60 tumours (73%) (FIG. 11A). TFF1 was absent in normal pancreas, but was expressed in 43/60 (72%) of PDACs (FIG. 11B). While no LYVE1 expression was seen in any of the cancer cells, it was seen in scarce lymphatic vessels in eight PDAC tissues (FIG. 11C). Next, the levels of all three biomarkers was measured in urines from seven PDAC patients for whom samples were collected prior to and after surgery (FIG. 11D). In all patients, levels of LYVE1 and REG1A decreased after surgery, and this was also seen in six out of seven patients for TFF1 (except for Patient 1, where the first post-surgical urine sample was collected tour months after the procedure), likely due to substantial loss of tumour mass after surgery.

Finally, as several reports have indicated that CA19.9 is also present in urine and can be used for cancer diagnosis, and was even superior to blood CA19.9 in some cases, Ca19.9 levels in urine samples were measured and compared them to matched plasma CA19.9. Urine CA19.9 did not prove useful in differentiating PDAC from CP and healthy urines in this case (data not shown).

PDAC is one of the most challenging cancers to detect; the majority of patients thus present at an advanced stage of the disease. Hence less than 20% of PDAC patients undergo potentially curative surgery, while the remainder can only be offered palliative treatment. Here, a three-biomarker urine panel is described that discriminates early stage PDAC patients from healthy subjects with high accuracy. A diagnostic test based on urine specimens was developed as this body fluid has several advantages over blood: it is far less complex, provides an 'inert' and stable matrix for analysis, and can be repeatedly and non-invasively sampled in sufficient volumes. So far, more than 2,300 proteins have been detected in urine, of which at least a third are of a systemic origin. As an ultrafiltrate of blood, it can be expected that at least some of the biomarkers will be found in higher concentration in urine than in blood.

When combined, REG1A and TFF1, LYVE1 form a powerful urinary panel that can detect patients with stages I-II PDAC, with over 90% accuracy. The exploratory analyses suggest that when combined with CA19.9, accuracy may be increased. In addition, the panel may prove useful in discriminating patient in stages I-IIA from healthy ones.

Being completely non-invasive and inexpensive, this urine screening test could, when coupled with timely surgical intervention, lead to a much improved outcome in patients with high-risk of developing pancreatic adenocarcinoma.

The invention claimed is:

1. A method of testing comprising determining concentrations of Lymphatic vessel endothelial hyaluronan receptor 1 (LYVE1) protein, Regenerating islet-derived 1 (REG1) protein, and Trefoil factor 1 (TFF1) protein, in a urine sample, wherein the REG1 protein is regenerating islet-derived 1A (REG1A) and/or regenerating islet-derived 1B (REG1B), by contacting the urine sample to an assay comprising:
one enzyme-linked immunosorbent assay (ELISA) for measuring the concentrations of LYVE1, REG1 and TFF1, or
two enzyme-linked immunosorbent assays (ELISAs) for measuring the concentrations of LYVE1, REG1 and TFF1, or
three enzyme-linked immunosorbent assays (ELISAs) for measuring the concentrations of LYVE1, REG1 and TFF1.

2. The method according to claim 1, wherein the determining step is carried out using an antibody that specifically binds to LYVE1, an antibody that specifically binds to REG1, and an antibody that specifically binds to TFF1.

3. The method according to claim 1, wherein the urine sample is from a human subject having or suspected of having pancreatic ductal adenocarcinoma (PDAC).

4. The method according to claim 3, wherein the pancreatic ductal adenocarcinoma is stage I or stage II pancreatic ductal adenocarcinoma.

5. The method of claim 1, wherein the method provides differential diagnosis distinguishing between stage I pancreatic ductal adenocarcinoma (PDAC) and a healthy patient, between stage I PDAC and chronic pancreatitis (CP), or between stage I PDAC and a later stage of PDAC.

6. The method of claim 1, further comprising the step of comparing the level of expression or concentration of one or more miRNAs with a reference.

7. The method of claim 6, wherein the reference is a biological sample from a healthy patient.

8. The method of claim 1, further comprising determining concentration of CA19.9 protein.

9. The method of claim 1, wherein the determining step is carried out using the assay, and the assay comprises one ELISA for measuring the concentrations of LYVE1, REG1 and TFF1, and wherein the one ELISA comprises an antibody that specifically binds to LYVE1, an antibody that specifically binds to REG1, and an antibody that specifically binds to TFF1.

10. The method of claim 9, wherein the one ELISA for measuring the concentration of LYVE1, REG1 and TFF1 further comprises an antibody that specifically binds to creatinine for measuring concentration of creatinine and the method further comprises determining the concentration of creatinine.

11. The method of claim 1, wherein the determining step is carried out using the assay, and the assay comprises three separate ELISAs for measuring the concentration of LYVE1, REG1 and TFF1, wherein the three separate ELISAs comprises a first ELISA comprising an antibody that specifically binds to LYVE1, a second ELISA comprising an antibody that specifically binds to REG1, and a third ELISA comprising an antibody that specifically binds to TFF1.

12. The method of claim 11, wherein the assay further comprises a fourth separate ELISA comprising an antibody that specifically binds to creatinine and the method further comprises determining concentration of creatinine.

13. The method according to claim 11, wherein the sample is from a human subject having or suspected of having PDAC.

14. The method according to claim 11, wherein the pancreatic ductal adenocarcinoma is stage I or stage II pancreatic ductal adenocarcinoma.

15. The method of claim 11, wherein the method provides differential diagnosis distinguishing between stage I PDAC and a healthy patient, between stage I PDAC and chronic pancreatitis (CP), or between stage I PDAC and a later stage of PDAC.

16. The method of claim 11, further comprising comparing the concentration of each protein with a reference for each protein.

17. The method of claim 16, wherein the reference is a biological sample from a healthy patient.

18. The method of claim 11, further comprising determining the level of expression or concentration of CA19.9 protein.

19. The method of claim 11, wherein the three separate ELISAs are provided in separate kits.

20. The method of claim 1, wherein the determining step is carried out using the assay, and the assay comprises two ELISAs for measuring the concentration of LYVE1, REG1 and TFF1 comprising an antibody that specifically binds to LYVE1, an antibody that specifically binds to REG1, and an antibody that specifically binds to TFF1.

21. The method of claim 20, wherein the assay further comprises an ELISA comprising an antibody that specifically binds to creatinine and the method further comprises determining concentration of creatinine.

\* \* \* \* \*

SEQUENCE LISTING

<160> NUMBER OF SEQ ID NOS: 4

<210> SEQ ID NO 1
<211> LENGTH: 322
<212> TYPE: PRT
<213> ORGANISM: Homo sapiens

<400> SEQUENCE: 1

Met Ala Arg Cys Phe Ser Leu Val Leu Leu Thr Ser Ile Trp Thr
1               5                   10                  15

Thr Arg Leu Leu Val Gln Gly Ser Leu Arg Ala Glu Glu Leu Ser Ile
            20                  25                  30

Gln Val Ser Cys Arg Ile Met Gly Ile Thr Leu Val Ser Lys Lys Ala
            35                  40                  45

Asn Gln Gln Leu Asn Phe Thr Glu Ala Lys Glu Ala Cys Arg Leu Leu
        50                  55                  60

Gly Leu Ser Leu Ala Gly Lys Asp Gln Val Glu Thr Ala Leu Lys Ala
65                  70                  75                  80

Ser Phe Glu Thr Cys Ser Tyr Gly Trp Val Gly Asp Gly Phe Val Val
                85                  90                  95

Ile Ser Arg Ile Ser Pro Asn Pro Lys Cys Gly Lys Asn Gly Val Gly
            100                 105                 110

Val Leu Ile Trp Lys Val Pro Val Ser Arg Gln Phe Ala Ala Tyr Cys
            115                 120                 125

Tyr Asn Ser Ser Asp Thr Trp Thr Asn Ser Cys Ile Pro Glu Ile Ile
        130                 135                 140

Thr Thr Lys Asp Pro Ile Phe Asn Thr Gln Thr Ala Thr Gln Thr Thr
145                 150                 155                 160

Glu Phe Ile Val Ser Asp Ser Thr Tyr Ser Val Ala Ser Pro Tyr Ser
                165                 170                 175

Thr Ile Pro Ala Pro Thr Thr Thr Pro Pro Ala Pro Ala Ser Thr Ser
            180                 185                 190

Ile Pro Arg Arg Lys Lys Leu Ile Cys Val Thr Glu Val Phe Met Glu
            195                 200                 205

Thr Ser Thr Met Ser Thr Glu Thr Glu Pro Phe Val Glu Asn Lys Ala
210                 215                 220

Ala Phe Lys Asn Glu Ala Gly Phe Gly Gly Val Pro Thr Ala Leu
225                 230                 235                 240

Leu Val Leu Ala Leu Leu Phe Phe Gly Ala Ala Ala Gly Leu Gly Phe
            245                 250                 255

Cys Tyr Val Lys Arg Tyr Val Lys Ala Phe Pro Phe Thr Asn Lys Asn
            260                 265                 270

Gln Gln Lys Glu Met Ile Glu Thr Lys Val Val Lys Glu Glu Lys Ala
        275                 280                 285

Asn Asp Ser Asn Pro Asn Glu Glu Ser Lys Lys Thr Asp Lys Asn Pro
        290                 295                 300

Glu Glu Ser Lys Ser Pro Ser Lys Thr Thr Val Arg Cys Leu Glu Ala
305                 310                 315                 320

Glu Val

<210> SEQ ID NO 2
<211> LENGTH: 166
<212> TYPE: PRT
<213> ORGANISM: Homo sapiens

<400> SEQUENCE: 2

```
Met Ala Gln Thr Ser Ser Tyr Phe Met Leu Ile Ser Cys Leu Met Phe
1               5                   10                  15

Leu Ser Gln Ser Gln Gly Gln Glu Ala Gln Thr Glu Leu Pro Gln Ala
                20                  25                  30

Arg Ile Ser Cys Pro Glu Gly Thr Asn Ala Tyr Arg Ser Tyr Cys Tyr
            35                  40                  45

Tyr Phe Asn Glu Asp Arg Glu Thr Trp Val Asp Ala Asp Leu Tyr Cys
        50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Gly Thr Asp Asp Phe
                85                  90                  95

Asn Val Trp Ile Gly Leu His Asp Pro Lys Lys Asn Arg Arg Trp His
                100                 105                 110

Trp Ser Ser Gly Ser Leu Val Ser Tyr Lys Ser Trp Gly Ile Gly Ala
            115                 120                 125

Pro Ser Ser Val Asn Pro Gly Tyr Cys Val Ser Leu Thr Ser Ser Thr
        130                 135                 140

Gly Phe Gln Lys Trp Lys Asp Val Pro Cys Glu Asp Lys Phe Ser Phe
145                 150                 155                 160

Val Cys Lys Phe Lys Asn
                165

<210> SEQ ID NO 3
<211> LENGTH: 166
<212> TYPE: PRT
<213> ORGANISM: Homo sapiens

<400> SEQUENCE: 3

Met Ala Gln Thr Asn Ser Phe Phe Met Leu Ile Ser Ser Leu Met Phe
1               5                   10                  15

Leu Ser Leu Ser Gln Gly Gln Glu Ser Gln Thr Glu Leu Pro Asn Pro
                20                  25                  30

Arg Ile Ser Cys Pro Glu Gly Thr Asn Ala Tyr Arg Ser Tyr Cys Tyr
            35                  40                  45

Tyr Phe Asn Glu Asp Pro Glu Thr Trp Val Asp Ala Asp Leu Tyr Cys
        50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Ser Thr Asp Asp Ser
                85                  90                  95

Asn Val Trp Ile Gly Leu His Asp Pro Lys Lys Asn Arg Arg Trp His
                100                 105                 110

Trp Ser Ser Gly Ser Leu Val Ser Tyr Lys Ser Trp Asp Thr Gly Ser
            115                 120                 125

Pro Ser Ser Ala Asn Ala Gly Tyr Cys Ala Ser Leu Thr Ser Cys Ser
        130                 135                 140

Gly Phe Lys Lys Trp Lys Asp Glu Ser Cys Glu Lys Lys Phe Ser Phe
145                 150                 155                 160

Val Cys Lys Phe Lys Asn
                165

<210> SEQ ID NO 4
<211> LENGTH: 84
<212> TYPE: PRT
```

```
<213> ORGANISM: Homo sapiens

<400> SEQUENCE: 4

Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
            35                  40                  45

Ser Gln Cys Ala Asn Lys Gly Cys Cys Phe Asp Asp Thr Val Arg Gly
    50                  55                  60

Val Pro Trp Cys Phe Tyr Pro Asn Thr Ile Asp Val Pro Pro Glu Glu
65                  70                  75                  80

Glu Cys Glu Phe
```